US011286463B2

(12) United States Patent
Greco et al.

(10) Patent No.: US 11,286,463 B2
(45) Date of Patent: Mar. 29, 2022

(54) REPROGRAMMING OF AGED ADULT STEM CELLS

(71) Applicant: Advanced Regen Medical Technologies, LLC, Montclair, NJ (US)

(72) Inventors: Steven J. Greco, Montclair, NJ (US); Vincent C. Giampapa, Montclair, NJ (US)

(73) Assignee: Advanced ReGen Medical Technologies, LLC, Houston, TX (US)

(*) Notice: Subject to any disclaimer, the term of this patent is extended or adjusted under 35 U.S.C. 154(b) by 0 days.

(21) Appl. No.: 14/922,353

(22) Filed: Oct. 26, 2015

(65) Prior Publication Data

US 2016/0108370 A1   Apr. 21, 2016

Related U.S. Application Data

(63) Continuation-in-part of application No. 13/785,691, filed on Mar. 5, 2013, now abandoned.

(60) Provisional application No. 61/608,480, filed on Mar. 8, 2012.

(51) Int. Cl.
  *C12N 5/074*  (2010.01)
  *A61K 35/12*  (2015.01)

(52) U.S. Cl.
  CPC ............ *C12N 5/0696* (2013.01); *A61K 35/12* (2013.01); *C12N 2500/84* (2013.01)

(58) Field of Classification Search
  CPC .............................. C12N 5/0696; A61K 35/12
  See application file for complete search history.

(56) References Cited

U.S. PATENT DOCUMENTS

| | | | |
|---|---|---|---|
| 2,984,164 | A | 5/1961 | Melle |
| 3,083,939 | A | 4/1963 | Gallagher, Jr. |
| 3,122,333 | A | 2/1964 | Steele et al. |
| 3,436,081 | A | 4/1969 | Ungar |
| 8,257,973 | B2 | 9/2012 | Park et al. |
| 8,747,915 | B1 | 6/2014 | Giampapa |
| 8,945,558 | B2 | 2/2015 | Kobara |
| 9,828,603 | B2 | 11/2017 | Marbán et al. |
| 9,994,814 | B2 | 6/2018 | Giampapa |
| 10,717,931 | B2 | 7/2020 | Greco et al. |
| 10,772,911 | B2 | 10/2020 | Greco et al. |
| 2002/0033370 | A1 | 3/2002 | Bainbridge et al. |
| 2002/0046975 | A1 | 4/2002 | Langley et al. |
| 2004/0199935 | A1 | 10/2004 | Chapman |
| 2005/0158285 | A1 | 7/2005 | Giampapa |
| 2006/0188986 | A1 | 8/2006 | Millar et al. |
| 2007/0025973 | A1 | 2/2007 | Fitzsimmons et al. |
| 2007/0196918 | A1 | 8/2007 | Sayre et al. |
| 2008/0213812 | A1 | 9/2008 | Andrews et al. |
| 2008/0260704 | A1 | 10/2008 | Riordan et al. |
| 2008/0268429 | A1 | 10/2008 | Pietrzkowski |
| 2009/0011004 | A1 | 1/2009 | Lutz et al. |
| 2009/0317369 | A1 | 12/2009 | Hosoda et al. |
| 2009/0318345 | A1 | 12/2009 | Fibbe et al. |
| 2010/0273255 | A1 | 10/2010 | Tuschi et al. |
| 2011/0003008 | A1 | 1/2011 | Lim |
| 2011/0177054 | A1 | 7/2011 | Gibbings et al. |
| 2011/0258716 | A1 | 10/2011 | Baltimore et al. |
| 2011/0300112 | A1 | 12/2011 | Marbán et al. |
| 2012/0093385 | A1 | 4/2012 | Yokosawa et al. |
| 2012/0093885 | A1 | 4/2012 | Sahoo et al. |
| 2012/0253102 | A1 | 10/2012 | Marbán et al. |
| 2012/0258093 | A1 | 10/2012 | Butler-Browne et al. |
| 2012/0321723 | A1 | 12/2012 | Bruno et al. |
| 2013/0017176 | A1 | 1/2013 | Hosoda et al. |
| 2013/0143314 | A1 | 6/2013 | Shiels et al. |
| 2013/0177593 | A1 | 7/2013 | Gunn et al. |
| 2013/0195899 | A1 | 8/2013 | Ichim et al. |
| 2013/0209528 | A1 | 8/2013 | Levi et al. |
| 2013/0236428 | A1 | 9/2013 | Giampapa |
| 2013/0302285 | A1 | 11/2013 | Fong et al. |
| 2013/0336935 | A1 | 12/2013 | Niedernhofer et al. |

(Continued)

FOREIGN PATENT DOCUMENTS

| | | |
|---|---|---|
| CA | 2845280 | 2/2012 |
| CN | 102573856 | 7/2012 |

(Continued)

OTHER PUBLICATIONS

Rathore (2011, Preparative Biochemistry and Biotechnology, 41:398-421).*
Conboy, Irina M. et al, "Rejuvenation of aged progenitor cells by exposure to a young systemic environment", Nature, vol. 433, No. 7027, Feb. 17, 2005, pp. 760-764.
Supplementary European Search Report, Application No. 13757017.2, dated Jul. 7, 2015.
Halley-Stott, Development, 2013, 140:2468-2471.
Singhal, 2010, Cell, 141:943-955.
Simonsson, 2004, Nature Cell Biology, 6:984-990.
Rando, Thomas A., et al., "Aging Rejuvenation, and Epigenetic Reprogramming: Resetting the Aging Clock", Cell, Jan. 20, 2012, vol. 148, pp. 46-57, Elsevier Inc.
Sun, Yun, et al., "Rescuing replication and osteogenesis of aged mesenchymal stem cells by exposure to a young extracellular matrix," The FASEB Journal, May 2011, vol. 25, No. 5, pp. 1474-1485.

(Continued)

*Primary Examiner* — Valarie E Bertoglio
(74) *Attorney, Agent, or Firm* — Knobbe Martens Olson & Bear LLP

(57) ABSTRACT

A method comprising (a) obtaining young adult stem cells (YASC) from a first subject; (b) lysing the YASC to generate a lysate comprising an intracellular matrix (ICM) and other cellular components; (c) filtering the lysate through a filter having a membrane size of equal to or less than 0.4 micron to obtain a filtrate; and (d) applying the filtrate to a culture of aged adult stem cells (AASC) for a time period ranging from about 24 hours to about 30 days to generate a reprogrammed AASC (R-AASC) wherein the AASC were obtained from a second subject and wherein the R-AASC when infused into a breast cancer stem model results in a reduced number of breast cancer cells in bone marrow in comparison to a breast cancer stem model having AASC that have not been reprogrammed.

18 Claims, 22 Drawing Sheets

(56) References Cited

U.S. PATENT DOCUMENTS

| | | |
|---|---|---|
| 2014/0004601 A1 | 1/2014 | Lim |
| 2014/0031256 A1 | 1/2014 | Lim |
| 2014/0088006 A1 | 3/2014 | Tsyrolva et al. |
| 2014/0120066 A1 | 5/2014 | Yeghiazarians et al. |
| 2014/0121171 A1 | 5/2014 | Muñoz-Canóves et al. |
| 2014/0127284 A1 | 5/2014 | Cheresh |
| 2015/0023935 A1 | 1/2015 | Giampapa |
| 2015/0174166 A1 | 6/2015 | Giampapa |
| 2015/0203844 A1 | 7/2015 | Marbán et al. |
| 2015/0273113 A1 | 10/2015 | Marbán et al. |
| 2015/0328263 A1 | 11/2015 | Kaushal |
| 2015/0367063 A1 | 12/2015 | Kimura |
| 2016/0108370 A1 | 4/2016 | Greco et al. |
| 2016/0145571 A1 | 5/2016 | Giampapa |
| 2016/0243171 A1 | 8/2016 | Shiels et al. |
| 2017/0087087 A1 | 3/2017 | Leonard et al. |
| 2017/0107581 A1 | 4/2017 | Kawauchi et al. |
| 2017/0130275 A1 | 5/2017 | Kondou et al. |
| 2017/0173076 A1 | 6/2017 | Greco et al. |
| 2017/0275699 A1 | 9/2017 | Kawauchi et al. |
| 2017/0290860 A1 | 10/2017 | Marbán et al. |
| 2017/0304368 A1 | 10/2017 | Marbán et al. |
| 2017/0314019 A1 | 11/2017 | Greco et al. |
| 2018/0100149 A1 | 4/2018 | Marbán et al. |
| 2018/0360878 A1 | 12/2018 | Giampapa |
| 2018/0371465 A1 | 12/2018 | Hinkle |
| 2019/0000888 A1 | 1/2019 | Marbán et al. |

FOREIGN PATENT DOCUMENTS

| | | |
|---|---|---|
| CN | 109475645 | 3/2019 |
| EP | 1 361 268 | 11/2003 |
| EP | 2 687 219 | 1/2014 |
| EP | 2 823 039 | 1/2015 |
| EP | 2 984 164 | 2/2016 |
| EP | 3 083 939 | 10/2016 |
| EP | 3 122 333 | 2/2017 |
| EP | 3 436 081 | 2/2019 |
| JP | 2013-504542 | 2/2013 |
| JP | 2015-524844 | 8/2015 |
| JP | 2017510582 A | 4/2017 |
| JP | 6353073 B2 | 7/2018 |
| JP | 6471302 | 2/2019 |
| KR | 10-2008-0049917 | 6/2008 |
| KR | 20170139701 A | 5/2017 |
| TW | 201739458 A | 11/2017 |
| WO | 2004048555 | 6/2004 |
| WO | WO 2006/007529 | 1/2006 |
| WO | WO 2006/052925 | 5/2006 |
| WO | 2007016245 | 2/2007 |
| WO | WO 2007/109223 | 9/2007 |
| WO | WO 2008/066330 | 6/2008 |
| WO | WO 2008/103135 A2 | 8/2008 |
| WO | WO 2009/011546 | 1/2009 |
| WO | 2009086425 | 7/2009 |
| WO | WO 2009/105044 | 8/2009 |
| WO | WO 2011/029903 | 3/2011 |
| WO | WO 2012/020307 | 2/2012 |
| WO | WO 2012/149557 | 11/2012 |
| WO | WO 2012/162741 | 12/2012 |
| WO | WO 2013/048734 | 4/2013 |
| WO | WO 2013066368 | 5/2013 |
| WO | 20130134513 | 9/2013 |
| WO | WO 2013/170170 | 11/2013 |
| WO | WO 2014/013258 | 1/2014 |
| WO | WO 2014028493 A2 | 2/2014 |
| WO | WO 2014028493 A3 | 2/2014 |
| WO | WO 2014/036429 | 3/2014 |
| WO | WO 2014/053105 | 4/2014 |
| WO | WO 2014/125276 | 8/2014 |
| WO | WO 2014/169077 | 10/2014 |
| WO | WO 2015/022545 | 2/2015 |
| WO | WO 2015/052527 | 4/2015 |
| WO | WO 2015/073625 | 5/2015 |
| WO | WO 2015/085096 | 6/2015 |
| WO | WO 2015095794 | 6/2015 |
| WO | WO 2015/120150 | 8/2015 |
| WO | WO 2015/148534 | 10/2015 |
| WO | WO 2015/182781 A1 | 12/2015 |
| WO | WO 2015/190542 A1 | 12/2015 |
| WO | WO 2016/054591 | 4/2016 |
| WO | WO 2016/057560 | 4/2016 |
| WO | WO 2017/190000 | 4/2017 |
| WO | WO 2009/011546 | 1/2019 |
| WO | WO 2019/028223 | 2/2019 |
| WO | WO 2019/143847 A1 | 7/2019 |
| WO | WO 2020/190888 | 9/2020 |

OTHER PUBLICATIONS

Bougel, S. et al., "PAX5 activates the transcription of the human telomerase reverse transcriptase gene in B cells", J. Pathol. 2010, vol. 220, No. 1, pp. 87-96.

He, X. et al., "Human Fibroblast Reprogramming to Pluripotent Stem Cells Regulated by the miR19a/b-PTEN Axis" PLOS One, Apr. 16, 2014, vol. 9, No. 4, p. e95213.

Jurmeister, S. et al., "MicroRNA-200c represses migration and invasion of breast cancer cells by targeting actin-regulatory proteins FHOD1 and PPM1F", Mol. Cell. Biol., Feb. 2012, vol. 32, No. 3, pp. 633-651.

Lam et al., "siRNA Versus MiRNA as Therapeutics for Gene Silencing," Molecular Therapy—Nucleic Acids (2015) vol. 4: pp. 1-20.

Li, Zhonghan et al, "Small RNA-mediated regulation of iPS cell generation", EMBO Journal, Feb. 1, 2011, vol. 30, pp. 823-834.

Liang, J., et al., "MicroRNA-103a inhibits gastric cancer cell proliferation, migration and invasion by targeting c-Myb" Cell Proliferation, Dec. 22, 2014, vol. 48, No. 1, pp. 78-85.

Lu, D., et al., "The miR-155-PU.1 axis acts on Pax5 to enable efficient terminal B cell differentiation", J. Exp. Med., 2014, vol. 211, No. 11, pp. 2183-2198.

NCBI Reference Sequence No. NM_014634.3, "Homo sapiens protein phosphatase, Mg2+/Mn2+ dependent 1F (PPM1F), mRNA," Oct. 16, 2017, 9 pages.

NCBI Reference Sequence No. NM_016734.2, "Homo sapiens paired box 5 (PAX5), transcript variant 1, mRNA," Nov. 30, 2017, 12 pages.

NCBI Reference Sequence No. NR_030350.1, "Homo sapiens microRNA 619 (MIR619), microRNA," Jun. 26, 2017, 4 pages.

Niyazova et al., "The interaction of miRNAs with mRNAs of the cell cycle genes in lung cancer", Proceedings of the Moscow Conference on Computational Molecular Biology (MCCMB'15), Jul. 2015, XP55595996, 4 pages.

PPM1F Wikipedia downloaded from https ://en. wikipedia .org/ wiki/P PM 1 F on Sep. 9, 2019, pp. 1-5.

Rejenevie Therapeutics [rejenevie]. (published May 10, 2019). "FAQs for Patients: Restoration & Young Donors," [Video file]. Retrieved from https://youtu.be/GOm_Q5nTbPM, (transcript provided herewith) 1 page.

Rejenevie Therapeutics [rejenevie]. (published May 10, 2019). "FAQs for Patients: Okyanos & Post-Treatment Testing," [Video file]. Retrieved from https://youtu.be/YU-v4yic36l, (transcript provided herewith) 1 page.

Rejenevie Therapeutics [rejenevie]. (published May 10, 2019). "FAQs for Patients: Screening, Mobilization & Treatment," [Video file]. Retrieved from https://youtu.be/V3NIJ-emB1U, (transcript provided herewith) 1 page.

Rejenevie Therapeutics [rejenevie]. (published May 15, 2019). "The Science Behind Immune Restoration," [Video file]. Retrieved from https://youtu.be/alKFhloo-L4, (transcript provided herewith) 2 pages.

Rejenevie Therapeutics [rejenevie]. (published May 23, 2019). "The Science Behind the Transwell System," [Video file]. Retrieved from https://youtu.be/Y75UXv747IQ, (transcript provided herewith) 1 page.

Rejenevie Therapeutics [rejenevie]. (published Jun. 10, 2019). "10 Steps to Immune Restoration with Rejenevie," [Video file]. Retrieved from https://youtu.be/ulCaTgjXXf8, (transcript provided herewith) 2 pages.

(56) References Cited

OTHER PUBLICATIONS

Sugihara et al., "Carnosine induces intestinal cells to secrete exosomes that activate neuronal cells." PLOS ONE (2019) 14(5)e:0217394; pp. 1-17.
Suh, Mi-Ra, et al., "Human embryonic stem cells express a unique set of mircoRNAs" Development Biology, May 6, 2004, vol. 270, No. 2, pp. 488-498.
Tu, S.H. et al., "Protein phosphatase Mg2+/Mn2+ dependent 1F promotes smoking-induced breast cancer by inactivating phosphorylated-p53-induced signals," Oncotarget, Oct. 18, 2016, vol. 7, No. 47, pp. 77516-77531.
Yu, Bin et al., "Exosomes secreted from GATA-4 overexpressing mesenchymal stem calls serve as a reservoir of anti-apoptotic microRNAs for cardioprotection" International Journal of Cardiology, Dec. 23, 2014, vol. 182, pp. 349-360.
Yu, Ge et al., "MicroRNA-19a targets tissue factor to inhibit colon cancer cells migration and invasion" Molecular and Cellular Biochemistry, May 12, 2013, vol. 380, No. 1-2, pp. 239-247.
Zhang et al., "miR-1303 Targets Claudin-18 Gene to Modulate Proliferation and Invasion of Gastric Cancer Cells", Digestive Diseases and Sciences, vol. 59, No. 8, Mar. 20, 2014, pp. 1754-1763, XP55595270.
International Search Report and Written Opinion dated Jul. 26, 2013 for PCT/US2013/029633.
International Search Report and Written Opinion dated Aug. 26, 2014 for PCT/US2014/033564.
International Preliminary Report on Patentability dated Sep. 18, 2014 for PCT/US2013/029633.
International Search Report and Written Opinion dated Mar. 31, 2015 for PCT/US2014/071667.
International Preliminary Report on Patentability dated Oct. 22, 2015 for PCT/US2014/033564.
International Search Report and Written Opinion dated Jun. 30, 2015 for PCT/US2015/022285.
International Preliminary Report on Patentability dated Jun. 30, 2016 for PCT/US2014/071667.
International Preliminary Report on Patentability dated Oct. 6, 2016 for PCT/US2015/022285.
International Search Report and Written Opinion dated Sep. 12, 2017 for PCT/US2017/030117.
International Preliminary Report on Patentability dated Aug. 20, 2018 for PCT/US2017/030117.
International Search Report and Written Opinion dated May 8, 2019 for PCT/US2019/014061.
Extended European Search Report dated Jul. 7, 2015 for EP 13 757 017.2.
Extended European Search Report dated Oct. 26, 2016 for EP 14 782 619.2.
Extended European Search Report dated Apr. 13, 2017 for EP 14 871 789.5.
Extended European Search Report dated Oct. 26, 2017 for EP 15 768 892.0.
European Examination Report dated Nov. 23, 2017 for EP 14 782 619.2.
European Examination Report dated Feb. 12, 2018 for EP 14 571 789.5.
European Examination Report dated Nov. 6, 2018 for EP 15 768 892.0.
Partial Supplementary European Search Report dated Feb. 11, 2019 for EP 17 790 538.7.
Summons to Attend Oral Proceedings dated Feb. 11, 2019 for EP 14 782 619.2.
Canadian Office Action dated Oct. 17, 2016 for CA 2,911,692.
Canadian Office Action dated Oct. 10, 2017 for CA 2,911,692.
Canadian Office Action dated Aug. 27, 2019 for CA 3,023,468.
Korean Office Action dated Feb. 20, 2017 for KR 10-2015-7032122.
Korean Office Action dated Mar. 13, 2017 for KR 10-2015-7032122.
Korean Office Action dated Aug. 25, 2017 for KR 10-2015-7032122.
Korean Office Action dated Nov. 16, 2017 for KR 10-2015-7032122.
Japanese Office Action dated Dec. 19, 2017 for Japanese patent application JP 2016-0560872.
Taiwan Office Action dated Sep. 19, 2019 for Taiwan patent Application No. 106114364.
Ajijola et al., "Ventricular Tachycardia in Ischemic Heart Disease Substrates", Indian Heart Journal, 2014, pp. S24-S34, S28 & S30, vol. 66, Supplement 1.
Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts of Mdx Mice", Circulation Research, Dec. 5, 2014, vol. 115, No. 12, 24248, pp. E90-E91.
Archundia, A., et al., "Direct cardiac injection of G-CSF mobilized bone-marrow stem-cells improves ventricular function in old myocardial infarction," Life Sciences, Apr. 21, 2005, pp. 279-283, vol. 78, Elsevier Inc.
Baglio, S. R., et al,. "Mesenchymal stem cell secreted vesicles provide novel opportunities in (stem) cell-free therapy," Frontiers in Physiology, Sep. 6, 2012, pp. 1-11, vol. 3.
Baker, Darren J. et al., "Clearance of p16lnk4a-positive senescent cells delays ageing-associated disorders" Nature, Nov. 1, 2011, vol. 479, No. 7372, pp. 232-236.
Beelen, Dietrich W., et al., "Transplantation of Filgrastim-Mobilized Peripheral Blood Stem Cells From HLA-Identical Sibling or Alternative Family Donors in Patients With Hematologic Malignancies: A Prospective Comparison on Clinical Outcome, Immune Reconstitution, and Hematopoietic Chimerism," Blood, Dec. 15, 1997, pp. 4725-4735, vol. 90 No. 12, The American Society of Hematology.
Chen et al., "Mesenchymal Stem Cell Secretes Microparticles Enriched in Pre-MicroRNAs", Nucleic Acids Research, 2010, vol. 38, No. 1, pp. 215-224.
Chimenti et al., "Relative Roles of Direct Regeneration Versus Paracrine Effects of Human Cardiosphere-Derived Cells Transplanted Into Infarcted Mice", Circulation Research, Mar. 19, 2010, vol. 106, pp. 971-980.
De Bakker et al, "Slow Conduction in the Infarcted Human Heart 'Zigzag' Course of Activation", Circulation, Sep. 1993, pp. 915-926, vol. 88, No. 3.
De Couto et al., "Macrophages Mediate Cardioprotective Cellular Postconditioning in Acute Myocardial Infarction", The Journal of Clinical Investigation, Jul. 27, 2015, vol. 125, No. 8, pp. 3147-3162.
Grigorian-Shamagian et al., "Cardiac and Systemic Rejuvenation After Cardiosphere-Derived Cell Therapy in Senescent Rats", European Heart Journal, Oct. 14, 2017, vol. 38, No. 39, pp. 2957-2967.
Guan, X, et al., "miR-223 regulates adipogenic and osteogenic differentiation of mesenchymal stem cells through a CI EBPs/miR-223/FGFR2 regulatory feedback loop," Stem Cells, 2015, pp. 1589-1600, vol. 33, AlphaMed Press.
Hine et al., "NRF2 and the Phase II Response in Acute Stress Resistance Induced by Dietary Restriction", Journal of Clinical & Experimental Pathology, Jun. 19, 2012, vol. S4, No. 4, pp. 1-33.
Hoetzenecker, Konrad, et al., "Mononuclear cell secretome protects from experimental autoimmune myocarditis," European Heart Journal, Jan. 15, 2013, pp. 676-685, vol. 36, No. 11.
Hsieh, J.-Y., et al., "miR-146a-5p circuitry uncouples cell proliferation and migration, but not differentiation, in human mesenchymal stem cells," Nucleic Acids Research, 2013, pp. 9753-9763, vol. 41, No. 21.
Hu et al., "MicroRNA-210 as a Novel Therapy for Treatment of Ischemic Heart Disease", Circulation, Sep. 14, 2010, vol. 122, Supplement 11, S124-S131, pp. 17.
Ibrahim et al., "Exosomes as Critical Agents of Cardiac Regeneration Triggered by Cell Therapy", Stem Cell Reports, May 6, 2014, vol. 2, pp. 606-619.
Ibrahim, A., et al. "Exosomes: Fundamental Biology and Roles in Cardiovascular Physiology," Annu. Rev. Physiol., 78, 68-83, 2017.
Ibrahim et al., "Microrna-Containing Exosomes from Cardiosphere-Derived Cells Stimulate Cardiomyocyte Proliferation and Angiogenesis in Vitro, and Improve Functional Recovery after Myocardial Infarction in Mice", Circulation, 2012, vol. 126, Abs. 14697, pp. 4.

(56) References Cited

OTHER PUBLICATIONS

Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, Nov. 26, 2013, vol. 128, No. 22, Abs. 19186, pp. 2.

Iglesias, D. M., "Stem Cell Microvesicles Transfer Cystinosin to Human Cystinotic Cells and Reduce Cystine Accumulation in Vitro," PLOS ONE, Aug. 13, 2012, pp. 1-9, vol. 7, No. 8.

Jayawardena et al., MicroRNA-Mediated In Vitro and In Vivo Direct Reprogramming of Cardiac Fibroblasts to Cardiomyocytes, Circulation Research, 2012, vol. 110, No. 11, pp. 1465-1473.

Kamdar et al., "Dystrophin-Deficient Cardiomyopathy", Journal of the American College of Cardiology, 2016, vol. 67, No. 21, pp. 2533-2546.

Kim, Mi Jung, et al., "Age-related Deterioration of Hematopoietic Stem Cells," International Journal of Stem Cells, 2008, 99. 55-63, vol. 1, No. 1.

Kooijmans et al., "PEGylated and Targeted Extracellular Vesicles Display Enhanced Cell Specificity and Circulation Time", Journal of Controlled Release, 2016, vol. 224, pp. 77-85.

Kordelas, L., et aL, "MSC-derived exosomes: a novel tool to treat therapy-refractory graft-versus-host disease," Leukemia, Jan. 21, 2014, pp. 970-973, vol. 28, Macmillan Publishers Limited.

Kroschinsky, Frank, et al., "Single-dose pegfilgrastim for the mobilization of allogeneic CD34+ peripheral blood progenitor cells in healthy family and unrelated donors," Haematologica, Dec. 1, 2005, pp. 1665-1671, vol. 90, No. 12, Ferrata Storti Foundation.

Lai et al., "Exosome Secreted by MSC Reduces Myocardial Ischemia/Reperfusion Injury", Stem Cell Research, 2010, vol. 4, pp. 214-222.

Lavasani, Mitra, et al., "Muscle-derived stem/ progenitor cell dysfunction limits healthspan and lifespan in a murine progeria model," Nature Communications, Jan. 3, 2012, pp. 1-12, vol. 3, No. 608, Macmillan Publishers Limited.

Lee et al., "Intramyocardial Injection of Autologous Cardiospheres or Cardiosphere-Derived Cells Preserves Function and Minimizes Adverse Ventricular Remodeling in Pigs With Heart Failure Post-Myocardial Infarction", Journal of the American College of Cardiology, Jan. 25, 2011, vol. 57, No. 4, pp. 455-465.

Li et al., "Direct Comparison of Different Stem Cell Types and Subpopulations Reveals Superior Paracrine Potency and Myocardial Repair Efficacy with Cardiosphere-Derived Cells", Journal of American College of Cardiology, 2012, vol. 59, No. 10, pp. 942-953.

Li, Shu-Hong, et al., "Reconstitution of aged bone marrow with young cells repopulates cardiacresident bone marrow :derived progenitor cells and prevents cardiac dysfunction after a myocardial infarction", European Heart Journal, Apr. 16, 2012, pp. 1157-1167, vol. 34, No. 15.

McCullagh, Karl J A: "Can a young muscle's stem cell secretome prolong our lives?", Stem Cell Research & Therapy, vol. 3, May 2012.

Melamed, Doran, et al., "Aging and neoteny in the B lineage," Blood, 2012, vol. 120, No. 20.

Melief, Sara et al., "Multipotent stromal cells skew monocytes towards an anti-inflammatory interleukin-10-producing phenotype byproduction of interleukin-6," Haematologica, Jan. 24, 2013, 98(6): pp. 888-895.

Middleton et al., "Newt Cells Secrete Extracellular Vesicles with Therapeutic Bioactivity in Mammalian Cardiomyocetes", Journal of Extracellular Vesicles, 2018, vol. 7, pp. 1-15.

Mildner, Michael, et al., "Secretome of Peripheral Blood Mononuclear Cells Enhances Wound Healing," PLoS ONE, Mar. 22, 2013, pp. 1-8, vol. 8, No. 3.

Mittelbrunn, Maria, et al., "Unidirectional transfer of MicroRNA-loaded exosomes from T cell to antigen-presenting cells," Nature Communications, 2011, vol. 2, Article No. 282, 10 pages.

Ousaka et al., "Abstract 13881: Cardiac Progenitor Cell Infusion in Patients With Univentricular Heart Diseases in Heart Failure With Preserved Ejection Fraction", Circulation, Abstract 13881, 2015, vol. 132, <http://circ.ahajournals.org/content/132/Suppl_3/A13881.short>.

Ple et al., "The Repertoire and Features of Human Platelet microRNAs," (PLOS One (2012) vol. 7(12), article# e507 46, 14 pages). (Year: 2012).

Ratajczak M Z et al: "Pivotal role of paracrine effects in stem cell therapies in regenerative medicine: can we translate stem cell-secreted paracrine factors and microvesicles into better therapeutic strategies?", Leukemia (Basingstoke), vol. 26, No. 6, Jun. 2012.

Reiffel, James A., MD, FACC, "Ten Pearls for the Use of Antiarrhythmic Drugs for Atrial Fibrillation", Aug. 17, 2012, Retrieved from <http://www.acc.org/latest-in-cardiology/articles/2014/7/18/15/12/ten-pearls-for-the-use-of-antiarrhythmic-drugs-for-atrial-fibrillation>, pp. 17.

Scaria et al., "Host-Virus Genome Interactions: Marco Roles for MicroRNAs", Cellular Microbiology, 2007, vol. 9, No. 12, pp. 2784-2794.

Sharma et al., "Cardiosphere Derived Cells from Pediatric End-Stage Heart Failure Patients Have Enhanced Functional Activity due to the Heat Shock Response Regulating the Secretome", Stem Cells, Apr. 2015, pp. 1213-1229, vol. 33, No. 4.

Shen, Jinhui, et al., "Transplantation of mesenchymal stem cells from young donors delays aging in mice," Scientific Reports, 2011, vol. 1, Article No. 67, 8 pages.

Shmazaki, T., et al., "Heterochronic microRNAs in temporal specification of neural stem cells: application toward rejuvenation," NPJ Aging and Mechanisms of Disease, Jan. 7, 2016, pp. 1-6, vol. 2, No. 15014, Japanese Society of Anti-Aging Medicine/Macmillan Publishers Limited.

Tatsumi, Kimiko et al: "Granulocyte-Colony Stimulation Factor Increases Donor Mesenchymal Stem Cells in Bone Marrow and Their Mobilization Into Peripheral Circulation but Does Not Repair Dystrophic Heart After Bone Marrow Transplantation", Cire J, 2008 ; 72: 1351-1358.

Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, Mar. 12, 2013, vol. 61, No. 10, pp. 1108-1119.

U.S. Appl. No. 13/785,691, filed Mar. 5, 2013 including prosecution history.

U.S. Appl. No. 14/509,523, filed Oct. 8, 2014 including prosecution history.

U.S. Appl. No. 14/577,978, filed Dec. 19, 2014 including prosecution history.

U.S. Appl. No. 14/889,942, filed Nov. 9, 2015 including prosecution history.

U.S. Appl. No. 14/922,353, filed Oct. 26, 2015 including prosecution history.

U.S. Appl. No. 15/128,660, filed Sep. 23, 2016 including prosecution history.

U.S. Appl. No. 15/581,705, filed Apr. 28, 2017 including prosecution history.

U.S. Appl. No. 16/111,832, filed Aug. 24, 2018 including prosecution history.

U.S. Appl. No. 16/250,940, filed Jun. 17, 2019 including prosecution history.

Vrijsen et al., "Cardiomyocyte Progenitor Cell-Derived Exosomes Stimulate Migration of Endothelial Cells", Journal of Cellular and Molecular Medicine, 2010, vol. 14, No. 5, pp. 1064-1070.

Yu, B., et al., "Exosomes Derived from Mesenchymal Stem Cells," International Journal of Molecular Sciences, Mar. 17, 2014, pp. 4142-4157, vol. 15.

Au et al., "MIR-1303 Regulates Mycobacteria Induced Autophagy by Targeting Atg2B", PLOS One, 2016, vol. 11, No. 1, p. 14.

Blackman et al., "The Narrowing of the CD8 T Ceil Repertoire in Old Age", Current Opinion in Immunology, 2011, vol. 23, pp. 537-542.

Cho et al., "A New Mechanism for the Aging of Hematopoietic Stem Cells: Aging Changes the Clonal Composition of the Stem

(56) References Cited

OTHER PUBLICATIONS

Cell Compartment but not individual Stem Cells", Hematopoiesis and Stem Cells, Blood, Jun. 15, 2008, vol. 111, No. 12, pp. 5553-5561.

Das et al., "Differential Expression of miRNAs by Macrophages Infected with Virulent and Avirulent *Mycobacterium Tuberculosis*", Tuberculosis, vol. 93, Supplement, Dec. 1, 2013, pp. S47-S50.

Ghanbari et al., "Genetic Variations in MicroRNA-Binding Sites Affect MicroRNA-Mediated Regulation of Several Genes Associated with Cardio-Metabolic Phenotypes", Cardiovascular Genetics, Jun. 2015, vol. 8, pp. 473-486.

International Preliminary Report on Patentability and Whiten Opinion received in PCT Application No. PCT/US2020/023011, dated Sep. 30, 2021 in 9 pages.

International Search Report and Written Opinion received in PCT Application No. PCT/US2020/023011, dated Jul. 9, 2020 in 15 pages.

Lerebours et al., "miRNA Expression Profiling of Inflammatory Breast Cancer Identifies a 5-miRNA Signature Predictive of Breast Tumor Aggressiveness", International Journal of Cancer, 2013, vol. 133, No. 7, pp. 11.

Pang et al., "Age-Associated Changes in Human Hematopoietic Stem Ceils", Accepted Manuscript, Stanford University, 2017, pp. 19.

Pang et al., "Human Bone Marrow Hematopoietic Stem Cells are Increased in Frequency and Myeloid-Biased with Age", PNAS, Dec. 13, 2011, vol. 108, No. 50, pp. 20012-20017.

Qui et al., "Dysregulation of MALAT1 and MiR-619-5p as a Prognostic Indicatior in Advanced Colorectal Carcinoma", Oncology Letters, 2016, vol. 12, pp. 5036-5042.

Tchilian et al., "Altered CD45 Expression and Disease", Trends in Immunology, vol. 27, No. 3, Mar. 2006, pp. 146-153.

Zhu et al., "Comprehensive toxicity and immunogenicity studies reveal minimal effects in mice following sustained dosing of extracellular vesicles derived from HEK293T cells," Journal of Extracellular Vesicles, Published online Jun. 6, 2017, https://doi.org/10.1080/20013078.2017.1324730.

\* cited by examiner

| Gene Name | Gene Symbol | GenBank ID | Epigenetic Regulator (R) | Indirect Epigenetic Modulator (M) | ↑or↓ Expression (≥1.5 fold) with Reprogramming | ↑or↓ Expression (≥1.5 fold) with Reprogramming + Manumycin |
|---|---|---|---|---|---|---|
| C-abl oncogene 1, non-receptor tyrosine kinase | ABL1 | NM_005157 | R | | ↓ | No Change |
| V-akt murine thymoma viral oncogene homolog 1 | AKT1 | NM_005163 | R | | No Change | No Change |
| Aldehyde dehydrogenase 1 family, member A3 | ALDH1A3 | NM_000693 | R | | ↓ | No Change |
| Ataxia telangiectasia mutated | ATM | NM_000051 | | M | No Change | No Change |
| BMI1 polycomb ring finger oncogene | BMI1 | NM_005180 | | M | No Change | No Change |
| Calreticulin | CALR | NM_004343 | | | ↑ | No Change |
| Cyclin A2 | CCNA2 | NM_001237 | R | | No Change | No Change |
| Cyclin B1 | CCNB1 | NM_031966 | R | | No Change | No Change |
| Cyclin D1 | CCND1 | NM_053056 | | M | ↓ | No Change |
| Cyclin E1 | CCNE1 | NM_001238 | | M | No Change | No Change |
| CD44 molecule (Indian blood group) | CD44 | NM_000610 | | | ↓ | No Change |
| Cell division cycle 25 homolog C (S. pombe) | CDC25C | NM_001790 | R | | ↓ | ↑ |
| Cyclin-dependent kinase 2 | CDK2 | NM_001798 | | M | No Change | No Change |
| Cyclin-dependent kinase 4 | CDK4 | NM_000075 | | M | ↑ | No Change |

FIG. 3A

| A | B | C | D | E | F | G | H |
|---|---|---|---|---|---|---|---|
| Cyclin-dependent kinase 6 | CDK6 | NM_001259 | | M | No Change | No Change | |
| Cyclin-dependent kinase inhibitor 1A (p21, Cip1) | CDKN1A | NM_000389 | | M | No Change | No Change | |
| Cyclin-dependent kinase inhibitor 1B (p27, Kip1) | CDKN1B | NM_004064 | | | ↓ | No Change | |
| Cyclin-dependent kinase inhibitor 1C (p57, Kip2) | CDKN1C | NM_000076 | R | | ↓ | No Change | |
| Cyclin-dependent kinase inhibitor 2A (melanoma, p16, inhibits CDK4) | CDKN2A | NM_000077 | | M | ↓ | No Change | |
| Cyclin-dependent kinase inhibitor 2B (p15, inhibits CDK4) | CDKN2B | NM_004936 | R | | No Change | ↑ | |
| Cyclin-dependent kinase inhibitor 2C (p18, inhibits CDK4) | CDKN2C | NM_078626 | R | | ↓ | ↑ | |
| Cyclin-dependent kinase inhibitor 2D (p19, inhibits CDK4) | CDKN2D | NM_001800 | | M | ↓ | No Change | |
| CHK1 checkpoint homolog (S. pombe) | CHEK1 | NM_001274 | | M | No Change | ↑ | |
| CHK2 checkpoint homolog (S. pombe) | CHEK2 | NM_007194 | | M | ↑ | ↓ | |
| Cbp/p300-interacting transactivator, with Glu/Asp-rich carboxy-terminal domain, 2 | CITED2 | NM_006079 | R | | ↓ | No Change | |
| Collagen, type I, alpha 1 | COL1A1 | NM_000088 | | | ↓ | ↑ | |

FIG. 3B

| | | | | | | | |
|---|---|---|---|---|---|---|---|
| Collagen, type III, alpha 1 | COL3A1 | NM_000090 | | | ↓ | No Change | |
| Cellular repressor of E1A-stimulated genes 1 | CREG1 | NM_003851 | R | | ↑ | No Change | |
| E2F transcription factor 1 | E2F1 | NM_005225 | | M | No Change | No Change | |
| E2F transcription factor 3 | E2F3 | NM_001949 | | M | ↑ | No Change | |
| Early growth response 1 | EGR1 | NM_001964 | | | ↓ | No Change | |
| V-ets erythroblastosis virus E26 oncogene homolog 1 (avian) | ETS1 | NM_005238 | | M | ↓ | No Change | |
| V-ets erythroblastosis virus E26 oncogene homolog 2 (avian) | ETS2 | NM_005239 | | M | ↓ | No Change | |
| Fibronectin 1 | FN1 | NM_002026 | | | No Change | ↓ | |
| Growth arrest and DNA-damage-inducible, alpha | GADD45A | NM_001924 | | | ↓ | No Change | |
| Galactosidase, beta 1 | GLB1 | NM_000404 | | | ↑ | No Change | |
| Glycogen synthase kinase 3 beta | GSK3B | NM_002093 | R | | No Change | No Change | |
| V-Ha-ras Harvey rat sarcoma viral oncogene homolog | HRAS | NM_005343 | | | No Change | No Change | |

FIG. 3C

| | | | Q | R | S | T | U | V | W | X |
|---|---|---|---|---|---|---|---|---|---|---|
| Inhibitor of DNA binding 1, dominant negative helix-loop-helix protein | ID1 | NM_002165 | R | | ↓ | No Change |
| Interferon, gamma | IFNG | NM_000619 | | | ↓ | No Change |
| Insulin-like growth factor 1 (somatomedin C) | IGF1 | NM_000618 | | | ↑ | ↑ |
| Insulin-like growth factor 1 receptor | IGF1R | NM_000875 | R | | ↑ | No Change |
| Insulin-like growth factor binding protein 3 | IGFBP3 | NM_000598 | R | | ↑ | ↓ |
| Insulin-like growth factor binding protein 5 | IGFBP5 | NM_000599 | | | ↓ | No Change |
| Insulin-like growth factor binding protein 7 | IGFBP7 | NM_001553 | | | ↓ | No Change |
| Inhibitor of growth family, member 1 | ING1 | NM_005537 | R | | ↓ | No Change |
| Interferon regulatory factor 3 | IRF3 | NM_001571 | | | ↓ | No Change |
| Interferon regulatory factor 5 | IRF5 | NM_001098629 | | | ↑ | No Change |
| Interferon regulatory factor 7 | IRF7 | NM_001572 | | | ↓ | No Change |
| Mitogen-zctivated protein kinase kinase 1 | MAP2K1 | NM_002755 | | | No Change | No Change |
| Mitogen-activated protein kinase kinase 3 | MAP2K3 | NM_002756 | | | ↓ | No Change |
| Mitogen-activated protein kinase kinase 6 | MAP2K6 | NM_002758 | R | | ↓ | No Change |

FIG. 3D

| | | | Y Z AA AB AC AD AE AF | | | |
|---|---|---|---|---|---|---|---|
| Mitogen-activated protein kinase 14 | MAPK14 | NM_001315 | R | | No Change | No Change | |
| Mdm2 p53 binding protein homolog (mouse) | MDM2 | NM_002392 | | M | ↑ | No Change | |
| MORC family CW-type zinc finger 3 | MORC3 | NM_015358 | R | | No Change | No Change | |
| V-myc myelocytomatosis viral oncogene homolog (avian) | MYC | NM_002467 | R | | ↓ | No Change | |
| Nibrin | NBN | NM_002485 | | | No Change | No Change | |
| Nuclear factor of kappa light polypeptide gene enhancer in B-cells 1 | NFKB1 | NM_003998 | | | ↓ | No Change | |
| NADPH oxidase 4 | NOX4 | NM_016931 | | | ↓ | No Change | |
| Proliferating cell nuclear antigen | PCNA | NM_182649 | R | | No Change | No Change | |
| Phosphoinositide-3-kinase, catalytic, alpha polypeptide | PIK3CA | NM_006218 | R | | No Change | No Change | |
| Plasminogen activator, urokinase | PLAU | NM_002658 | R | | ↑ | No Change | |
| Protein kinase C, delta | PRKCD | NM_006254 | | | No Change | No Change | |
| Phosphatase and tensin homolog | PTEN | NM_000314 | | | ↑ | No Change | |
| Retinoblastoma 1 | RB1 | NM_000321 | | M | ↑ | No Change | |
| Retinoblastoma-like 1 (p107) | RBL1 | NM_002895 | R | | No Change | No Change | |
| Retinoblastoma-like 2 (p130) | RBL2 | NM_005611 | | M | ↓ | No Change | |

FIG. 3E

| | | | AK | AL | AM | AN |
|---|---|---|---|---|---|---|
| Serpin peptidase inhibitor, clade B (ovalbumin), member 2 | SERPINB2 | NM_002575 | R | | ↓ | ↓ |
| Serpin peptidase inhibitor, clade E (nexin, plasminogen) activator inhibitor type 1), member 1 | SERPINE1 | NM_000602 | R | | No Change | No Change |
| Sirtuin 1 | SIRT1 | NM_012238 | R | | ↓ | No Change |
| Superoxide dismutase 1, soluble | SOD1 | NM_000454 | | | ↓ | No Change |
| Superoxide dismutase 2, mitochondrial | SOD2 | NM_000636 | | | ↑ | No Change |
| Secreted protein, acidic, cysteine-rich (osteonectin) | SPARC | NM_003118 | R | | ↑ | No Change |
| T-box 2 | TBX2 | NM_005994 | | | ↓ | No Change |
| T-box 3 | TBX3 | NM_016569 | | | ↓ | No Change |
| Telomeric repeat binding factor 2 | TERF2 | NM_005652 | | | No Change | No Change |
| Telomerase reverse transcriptase | TERT | NM_198253 | | | ↓ | No Change |
| Transforming growth factor, beta 1 | TGFB1 | NM_000660 | R | | ↓ | No Change |
| Transforming growth factor beta 1 induced transcript 1 | TGFB1I1 | NM_015927 | | | ↓ | ↑ |
| Thrombospondin 1 | THBS1 | NM_003246 | | | ↓ | No Change |
| Tumor protein p53 | TP53 | NM_000546 | | M | ↑ | No Change |
| Tumor protein p53 binding protein 1 | TP53BP1 | NM_005657 | | | ↓ | No Change |
| Twist homolog 1 (Drosophila) | TWIST1 | NM_000474 | | M | ↓ | ↑ |
| Vimentin | VIM | NM_003380 | | | No Change | No Change |

FIG. 3F

| qPCR Analyses | Human CD45+ and/or CD105+ Populations (Includes Human Stem Cell Pools) | GAPDH+ Cells (Total Human Cell Pool) | Breast Cancer Cells (GFP+) |
|---|---|---|---|
| Bone Marrow -Non Restored | + | + | ++ |
| -Restored | ++ | ++ | + |
| Lung -Non Restored | - | - | - |
| -Restored | - | - | - |
| Liver -Non Restored | - | - | - |
| -Restored | - | - | - |
| Heart -Non Restored | - | - | - |
| -Restored | - | - | - |
| Kidney -Non Restored | - | - | - |
| -Restored | - | - | - |

| qPCR Analyses | Human CD45+ and/or CD105+ Populations (Includes Human Stem Cell Pools) | GAPDH+ Cells (Total Human Cell Pool) | Breast Cancer Cells (GFP+) |
|---|---|---|---|
| Bone Marrow -Non Restored | - | - | - |
| -Restored | - | - | - |
| Lung -Non Restored | - | - | - |
| -Restored | - | - | - |
| Liver -Non Restored | - | - | - |
| -Restored | - | - | - |
| Heart -Non Restored | - | - | - |
| -Restored | - | - | - |
| Kidney -Non Restored | - | - | - |
| -Restored | - | - | - |

| AASC | Peripheral Blood | | Bone Marrow | | | Other Tissues | | % Survival |
|---|---|---|---|---|---|---|---|---|
| | CD45 | BCC | CD45 | BCC | Hematopoiesis | CD45 | BCC | |
| 1-Month Endpoint | | | | | | | | |
| Non-Reprogrammed | None | None | Low | High | Low | None | None | 100 |
| Reprogrammed | None | None | High | Low | High | None | None | 100 |
| 12-Month Endpoint | | | | | | | | |
| Non-Reprogrammed | None | None | None | None | Low | None | None | 100 |
| Reprogrammed | None | None | None | None | High | None | None | 75 |

FIG. 17

REPROGRAMMING OF AGED ADULT STEM CELLS

REFERENCE TO RELATED APPLICATION

The present application is a continuation in part of U.S. patent application Ser. No. 13/785,691, filed Mar. 5, 2013, entitled "Reprogramming of Aged Adult Stem Cells," incorporated herein by reference.

TECHNICAL FIELD

The present disclosure generally relates to methodologies for the reprogramming of stem cells. More specifically this disclosure relates to the therapeutic utilization of these methodologies.

BACKGROUND

Adult stem cells lose functional quality and the ability to maintain tissue homeostasis with increasing age. This contributes to the natural age-related loss of function of the human body as well as contributes to the diseases of aging such as diabetes, immunological disorders, cardiovascular disease, and other age-related disease processes. An ongoing need exists for novel methodologies and therapies for addressing the diseases of aging.

SUMMARY

Disclosed herein is a method comprising (a) obtaining young adult stem cells (YASC) from a first subject; (b) lysing the YASC to generate a lysate comprising an intracellular matrix (ICM) and other cellular components; (c) filtering the lysate through a filter having a membrane size of equal to or less than 0.4 micron to obtain a filtrate; and (d) applying the filtrate to a culture of aged adult stem cells (AASC) for a time period ranging from about 24 hours to about 30 days to generate a reprogrammed AASC (R-AASC) wherein the AASC were obtained from a second subject and wherein the R-AASC when infused into a breast cancer stem model results in a reduced number of breast cancer cells in bone marrow in comparison to a breast cancer stem model having AASC that have not been reprogrammed.

Also disclosed herein is a method comprising (a) collecting young adult stem cells (YASC) from a first subject having a chronological age of less than about 40 years; (b) lysing the YASC to generate a mixture; (c) filtering the mixture through a size-selective membrane to produce a reprogramming solution; and (d) contacting the reprogramming solution with a culture of aged adult stem cells (AASC) for a time period of from about 24 hours to about 14 days to produce reprogrammed AASC (R-AASC) wherein the R-AASC have an increase in expression of calreticulin and galactosidase-β1 of equal to or greater than about 1.5 fold when compared to the AASC.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

FIGS. 3A, 3B, 3C, 3D, 3E, and 3F depict a descriptive list of genes used to test for aged adult stem cell (AASC) reprogramming.

FIG. 17 is a descriptive list of attributes used to test for AASC reprogramming.

DETAILED DESCRIPTION

Figure 1:
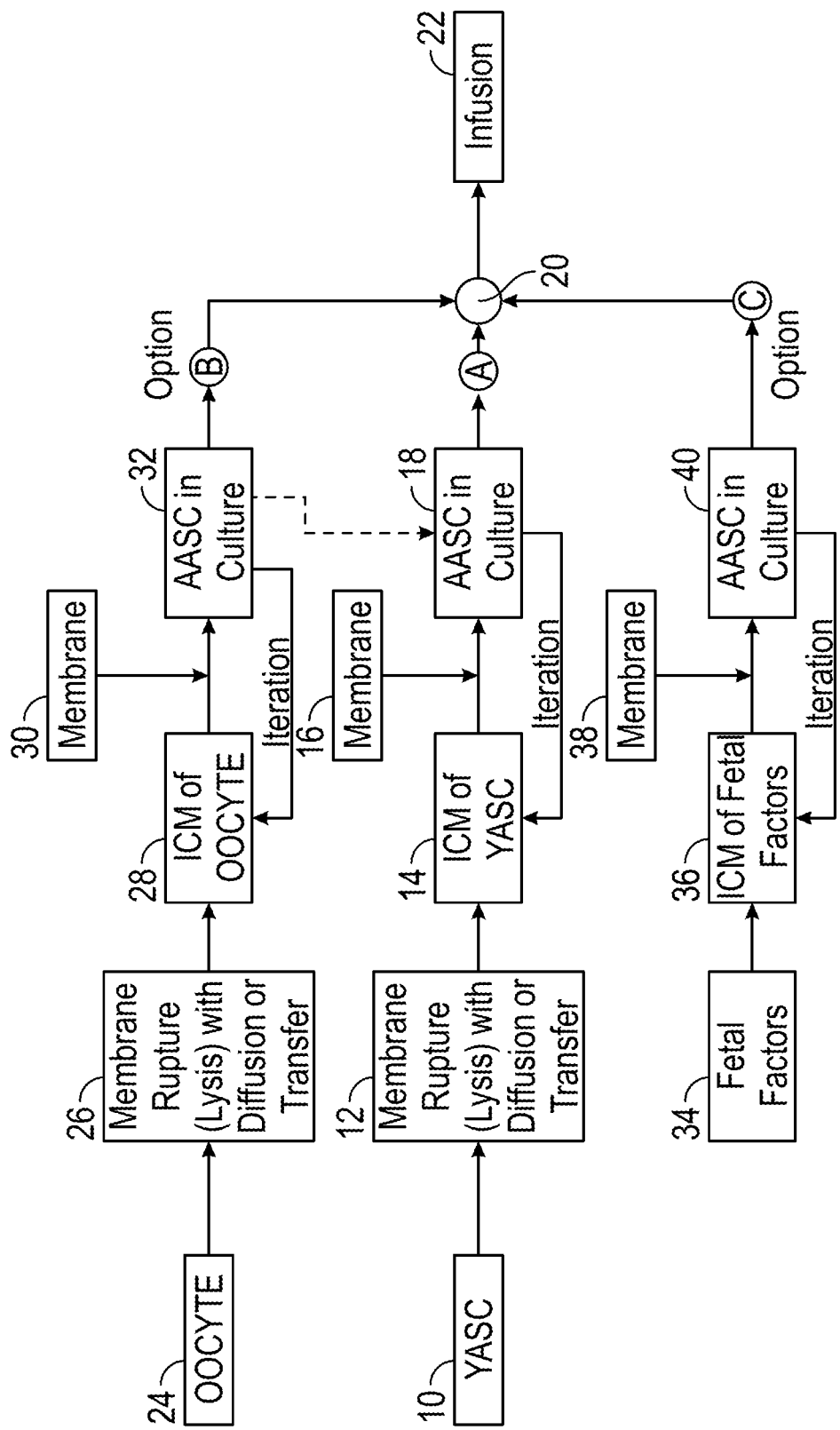
FIG. 1 is a conceptual flow diagram of embodiments of the present disclosure.

Disclosed herein are methods for the reprogramming of aged adult stem cells (AASC) utilizing exposure to the cellular components and/or factors of young adult stem cell (YASC) and/or human oocytes. Without wishing to be limited by theory, cellular aging is a manifestation of alterations in gene expression such that a YASC can have a general gene expression profile, designated α while an AASC can have a general gene expression profile designated ω. The methodologies disclosed herein may alter the gene expression patterns of an AASC ω such that the reprogrammed AASC have a gene expression profile designated β. The symbol β was chosen to indicate that the reprogrammed AASC prepared as disclosed herein have a gene expression profile resembling that of a YASC (α). Without wishing to be limited by theory, this may occur by "turning off" certain genes that are known to facilitate aging, while at the same time "turning back on" other genes known to promote youthful stem cell function and tissue homeostasis. The net effect of these alterations in gene expression is an improvement in functional quality at systemic levels. Hence, reprogramming is defined herein as the reactivation of youthful patterns of gene expression to evoke youthful stem cell function.

The methods of the present disclosure may first comprise the collection of AASCs and YASCs. The present disclosure contemplates reprogramming of AASCs for a first subject who is equal to or greater than about 40 years old, alternatively equal to or greater than about 45 years old, alternatively equal to or greater than about 50 years old, alternatively equal to or greater than about 55 years old, alternatively equal to or greater than about 60 years old, alternatively from about 40 years old to about 95 years old, alternatively from about 40 years old to about 75 years old, or alternatively from about 40 years old to about 60 years old. In some embodiments, the YASC are collected from a second subject having a chronological age of less than about 30 years, alternatively less than about 20 years, alternatively less than about 10 years, alternatively from about 10 years to about 29 years, alternatively from about 15 years to about 25 years or alternatively from about 20 years to about 25 years. In some embodiments, the AASCs, the YASCs, or both were previously collected and stored under conditions suitable to maintain viability of at least 50% of the cell sample for a period of time ranging from about 24 hours to about 20 years prior to being subjected to the methods of the present disclosure. Alternatively for a time period of from about 1 year to about 20 years, or alternatively for a time period of from about 10 years to about 20 years.

In an embodiment the first subject and second subject are the same. Alternatively the first subject and second subject are different. In some embodiments, the first subject and second subject are related by consanguinity. In an embodiment, the first subject has a disease, disorder, or unwanted medical condition absent from or undiagnosed in the second subject.

A method of the present disclosure comprises placing AASCs into standard culture media within a tissue culture dish chamber. The AASCs may have been previously mobilized into the peripheral blood following administration of a stem cell mobilizing agent and collected by cellular apheresis. Herein a stem cell mobilizing agent refers to a material able to induce the migration of stem cells from the bone marrow to the peripheral blood. Stem cell mobilization of the subjects may be performed by injection of Neupogen™ at a dose of 5 μg/kg. Mobilized peripheral blood mononuclear cells (PBMCs) containing AASCs or YASCs can then be collected by any suitable methodology such as apheresis after a suitable time period, for example from about 24 hours to about 5 days after administration of the stem cell mobilizing agent using any suitable methodology such as a cell separator. For example, a conventional apheresis program processes 18 L of blood at a flow rate of 50 to 100 mL per min. The apheresis procedures can be performed until the achievement of a suitable number of PBMCs such as equal to or greater than about $5 \times 10^6$ CD34$^+$ cells/kg.

In an embodiment, the methods of the present disclosure further comprise exposure of AASCs to the Intracellular Matrix (ICM) of the YASCs through placement of a transwell culture insert containing YASC into the tissue culture dish chamber. Mobilized PBMCs ($1 \times 10^7$) from the second subjects are added to the outer well of 12-well transwell cultures containing a 0.4 μM BD Falcon™ insert. Any membrane insert able to provide a cell-free filtrate to cultures of AASCs may be employed. In parallel, mobilized PBMCs ($1 \times 10^7$) from the first subjects are added to the inner well of the 12-well plate. Cells may then be cultivated in a suitable media (e.g., RPMI-1640 (Gibco) supplemented with 10% fetal calf serum (FCS) and β-mercaptoethanol (β-ME)) for a time period of the type disclosed herein (e.g., 8-weeks), under standard culture conditions (e.g., 50% media changed every 4 days).

During this cultivation period the ICM of the YASC may be released by the normal physiological rupture, lysis, and turnover of the cellular membrane. In an embodiment, the ICM comprises cellular components including but not limited to bioactive lipids, cytokines, chemokines, growth factors, exosomes and/or microvesicles which are released into the intercellular space and allowed to perfuse surrounding cells of the AASC by simple diffusion. As will be understood by one of ordinary skill in the art, and without wishing to be limited by theory, the soluble factors released by lysis of the YASC cell membrane are able to diffuse passively through the size-selective membrane of the transwell insert and initiate gene reprogramming effects in trans on the AASC in the lower culture chamber. The selective transwell membrane allows the passive diffusion of soluble factors such as for example and without limitation amino acids, bioactive lipids, chemokines, culture conditioned media, cytokines DNA, exosomes, growth factors, hormonal compounds, siRNA, microvesicles, microRNA, mRNA, aged human stem cells, human oocytes, human oocyte cell fluid components, peptides, polypeptides, RNA, and transcription factors but excludes larger biological material such as cells and apoptotic bodies that are greater than the pore size. Without wishing to be limited by theory, the present disclosure contemplates that one or more biomolecules such as cytokines, chemokines, growth factors, bioactive lipids, microvesicles and exosomes, which are contained intracellularly within the YASC as well as part of the cellular membrane itself, herein referred to as the intracellular matrix (ICM), function as reprogramming agents in the present disclosure.

For experiments investigating the contribution of exosomes as the membrane-permeable factors responsible for AASC reprogramming (i.e reprogramming agents), the exosomal inhibitor manumycin A (Sigma-Aldrich) can be added to the culture media at a final concentration of 5 μM at days 0 and 14 of the cultivation period.

The reprogramming of AASCs and alterations in gene expression profile (i.e. ω→β) occurs through direct exposure of the AASC to the ICM of YASC. For example, reprogramming occurs when the surface of the AASC is temporally-contacted with one or more soluble factors originating from the YASC. Such "contact" may be the described in one instance as one or more materials originating from the YASC touching the surface of the AASC. In some embodiments, the material contacting the AASC may contact some portion of the surface of the AASC and subsequently diffuse into the AASC, be transported into the AASC, or combinations thereof. Contacting of the material originating from the YASC with the AASC may be transient or permanent. YASC soluble factors, bioactive lipids, microvesicles and/or exosomes can be transferred directly into and through the cell membrane of the AASC through ligand-receptor mediated interactions, passive membrane transport and/or membrane fusion and endocytosis.

Once this transfer has occurred, the promoter regions of AASC genes may be engaged either by ectopically-transferred factors or ectopically-activated endogenous pathways, which epigenetically modify patterns of gene expression after an adequate time of exposure to the YASC. Without wishing to be limited by theory, epigenetic modification of age-related genes predominantly occurs through chemical modification of chromatin or promoter DNA, for example DNA methylation by DNA methyltransferases such as DNMT1 or histone acetylation by histone deacetylases such as SIRT1, or through chromatin remodeling by polycomb-group factors such as BMI1. This process can be described as a one-step process. In an embodiment, the reprogramming of at least 50% of the AASC occurs in a time period ranging from about 24 hours to about 30 days, alternatively from about 48 hours to about 14 days or alternatively from about 5 days to about 10 days.

In an alternative embodiment, the process can be accomplished in two or three steps. First, AASC are "primed" through brief exposure to the ICM of YASC or human oocytes via the same procedure as described for the one-step process, to initiate "gene imprinting erasure". The "erasure process" is accomplished because YASC and human oocytes contain soluble factors that can "erase" certain methylation patterns and other epigenetic marks of AASC. In this more comprehensive process, the AASC are first "genetically erased" through brief exposure to the ICM of YASC or human oocytes. In the second step, the "genetically erased" AASC are transferred into a fresh cell culture chamber dish and exposed to YASC for an extended period as described above for the one-step process.

The YASC soluble factors, microvesicles and bioactive lipids may interact with the genes of the AASC to initiate the reprogramming process at the epigenetic level. Nonlimiting examples of aging-related assays that may be used to confirm that functional reprogramming of AASC has occurred include measurements of beta-galactosidase (β-gal), telomerase (TERT) and number of colony forming units (CFU) produced by hematopoietic stem and progenitor cells. These measurements may be made prior to and after exposure to the YASC to document the efficiency of the reprogramming process.

The process disclosed above can alternatively be performed through exposing AASCs to the ICM of YASC or human fetal cells in transwell culture, but in the absence of the YASC or human fetal cells themselves. During this process the YASC supernatant or human fetal supernatant is first obtained by placing mobilized PBMCs ($1\times10^7$) from young human donors age 30 or younger or human fetal cells ($1\times10^7$) from fetal donors, respectively, within a culture well of a 12-well plate. Cells are then cultivated in RPMI-1640 (Gibco) supplemented with 10% fetal calf serum (FCS) and β-mercaptoethanol (β-ME) for 4-weeks and 50% media is collected and replaced every 4 days. Human fetal cells can be obtained from umbilical cord and include umbilical cord stem cells, or from amniotic fluid and include amniotic fluid stem cells.

Alternatively, YASC which can be applied to the AASC reprogramming model include but are not limited to: human mesenchymal stem cells, human adipose derived stem cells, human stromal cells, human skeletal muscle stem cells, human neural stem cells and human cardiac stem cells.

The presently disclosed method can also be utilized to produce a new class of clinically infusible cell products for promoting youthful function of the aging immune system to: 1) promote healthy aging, 2) treat immunological disorders and deficiencies, 3) treat HIV/AIDS patients, and 4) treat age-related disease.

The presently disclosed method can also be utilized to produce a new class of topically-applied clinical cell products to: 1) promote wound healing, 2) treat aging skin to prevent and remove wrinkles, and 3) treat skin cancers.

In an embodiment, the methods disclosed herein result in the production of a composition comprising AASC that have been reprogrammed to have an altered gene expression pattern. For example, the reprogrammed AASCs of the present disclosure (R-AASC) may be characterized by an alteration of greater than about 1.5 fold in the expression level of at least 10 genes selected from the group consisting of C-abl oncogene-1 non-receptor tyrosine kinase; V-akt murine thymona viral oncogene homolog 1; aldehyde dehydrogenase 1 family, member A3; Ataxia telangiectasia mutated; BMI1 polycomb ring finger oncogene; calrecticulin; cyclin A2; cyclin B1; cyclin D1; cyclin E1; CD44 molecule, cell division cycle 25 homolog C; cyclin-dependent kinase 2; cyclin-dependent kinase 4; cyclin-dependent kinase 6; cyclin-dependent kinase inhibitor 1A; cyclin-dependent kinase inhibitor 1B; cyclin-dependent kinase inhibitor 1C; cyclin-dependent kinase inhibitor 2A; cyclin-dependent kinase inhibitor 2B; cyclin-dependent kinase inhibitor 2C; and cyclin-dependent kinase inhibitor 2D when compared to the expression level of the AASC without reprogramming using the methodologies disclosed herein.

In an embodiment, the R-AASC may be administered to the first subject in amounts effective to treat one or more diseases, disorders, or unwanted medical conditions. In some embodiments, the R-AASC may be administered to a third subject in amounts effective to treat one or more diseases disorders or unwanted medical conditions. In an embodiment, the third subject is not related to the first subject by consanguinity. In an embodiment, the third subject is not related to the second subject by consanguinity.

In an embodiment, the R-AASC may be stored for a time period ranging from about 24 hours to about 10 years prior to being utilized. Alternatively from about 1 month to about 5 years, or alternatively from about 1 year to about 3 years.

EXAMPLES

The subject matter of the present disclosure having been generally described, the following examples are given as particular embodiments of the disclosure and to demonstrate the practice and advantages thereof. It is understood that the examples are given by way of illustration and are not intended to limit the specification or the claims to follow in any manner.

Example 1

Figure 2:
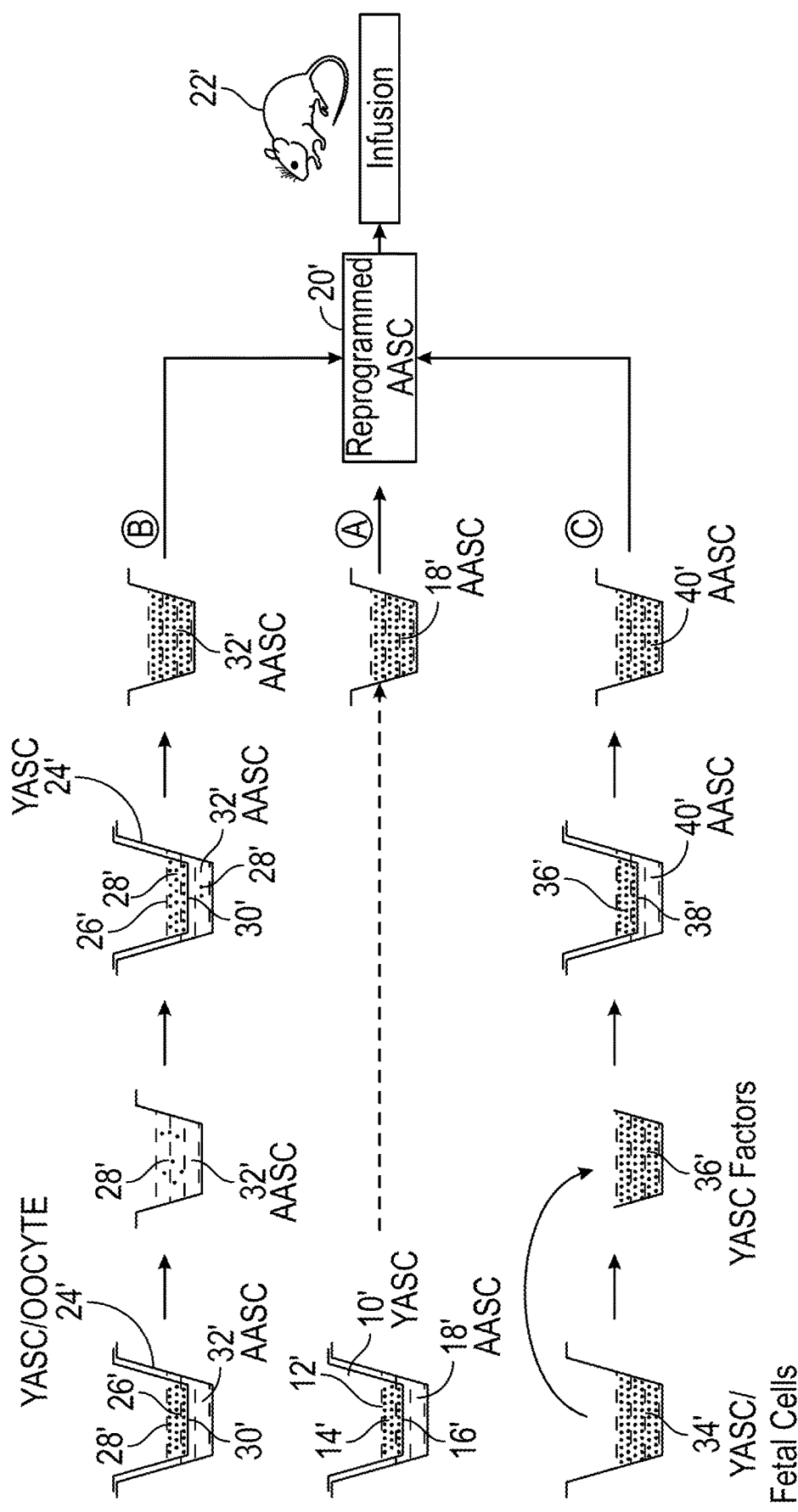
FIG. 2 is an alternate embodiment of the conceptual flow diagram of the present disclosure.

FIGS. 1 and 2 show conceptual flow diagrams to illustrate the method of AASC reprogramming, including the primary method involving the sole use of YASC, as well as two optional methods which entail the additional usage of oocytes or fetal factors. As depicted in the central workflow in FIGS. 1 and 2, the process begins with the collection of YASC 10 by cellular apheresis of Neupogen™-treated young donors. The collected YASC are then placed in transwell culture to enable the normal physiological rupture, lysis and turnover of the cellular membrane, whereby bioactive lipids or microvesicles are released 12. Such a process enables diffusion or transfer of the ICM as depicted in step 14. The ICM then passes through a size-selective 0.4 μm pore membrane 16, the purpose of which is to allow selective filtration of the desired intracellular components of the YASC. The ICM components passing through membrane 16 then diffuse through the culture media in the lower chamber and perfuse the AASC to be reprogrammed, shown at step 18. If this is the sole strategy employed in a given AASC reprogramming project, the culture of step 18 is collected at Step A, formulated at step 20 and infused, at step 22, as an autologous, allogeneic or xenogeneic transplant.

In the event that a priming step 24 is employed prior to the above-described steps 10 to 18, for purposes of "cleaning" some of the age-related epigenetic signatures characteristic of the AASC, the YASC or human oocyte is placed in transwell culture to enable the normal physiological rupture, lysis and turnover of the cellular membrane, whereby bioactive lipids or microvesicles are released as shown in step 26. Such a process enables diffusion or transfer of the ICM as depicted in step 28 and passes through membrane 30 to diffuse through the culture media in the lower chamber and perfuse the AASC 32 to be reprogrammed. Both steps 18 above and said step 32 may be reiterated relative to steps 14 and 28, respectively, several times in order to assure maximum reprogramming of the resultant cell product B.

As an alternative option, intended to equate the effectiveness of the present method, factors from YASC or human fetal cells 34 may first be separated from the cell cultures in order to isolate the ICM 36. The cell-free ICM composition is then added to transwell culture to pass through the membrane 38 and diffuse through the culture media in the lower chamber and perfuse the AASC 40 to be reprogrammed. The resultant reprogrammed stem cell formulation (step C) yields a reprogrammed cell product 20 that can be infused as an autologous, allogeneic or xenogeneic transplant.

Example 2

AASC reprogramming was carried out using the one-step process depicted in the middle workflow of FIGS. 1 and 2. Next, gene array studies were carried out using a commercially available qPCR array that contains probes for 84 genes reported to be linked to cellular aging, epigenetics and senescence. FIGS. 3A, 3B, 3C, 3D, 3E, and 3F depict a descriptive list of the genes used to test for AASC reprogramming. Of note, the array contains several aging-related biomarkers that can be utilized to confirm functional reprogramming of AASC, such as β-gal and TERT. The gene expression profiles of AASC were compared before and after AASC reprogramming. Prior to reprogramming, AASC have an elevated expression of most aging-related genes compared to after reprogramming. This gene panel can be utilized to test whether cellular reprogramming has occurred. Of note, a number of genes that were modulated after exposure to the ICM of YASC were epigenetic regulators, such as the histone deacetylase, SIRT1, or indirect epigenetic modulators, such as the chromatin remodeling factor, BMI1.

The nature of the YASC soluble ICM factors passing through the permeable membrane in the transwell culture experiments was also investigated. Specifically, transwell culture experiments were carried out in the presence or absence of manumycin. Manumycin, -[(1S,5S,6R)-5-hydroxy-5-[(1E,3E,5E)-7-[(2-hydroxy-5-oxo-1-cyclopenten-1-yl)amino]-7-oxo-1,3,5-heptatrien-1-yl]-2-oxo-7-oxabicyclo[4.1.0]hept-3-en-3-yl]-2E,4E,6R-trimethyl,2,4-decadienamide, is an antibiotic that acts as a potent and selective farnesyltransferase inhibitor. Manumycin is also known to inhibit the release of exosomes. AASC co-cultured with YASC in the presence of 5 μM manumycin displayed changes in gene expression levels compared to those observed in the absence of manumycin (FIGS. 3A-3F). These results suggest that microvesicles, specifically exosomes, play a role in the mechanism of AASC reprogramming.

Example 3

Nude female BALB/c mice can be infused through intravenous route with $10^7$ human AASC that have or have not undergone the reprogramming procedure described in the middle workflow of FIGS. 1 and 2. Nude mice can be utilized because the cells are human and will survive immune rejection, and thus are an apt model to see if reprogramming of AASC can promote endogenous immune and hematopoietic function.

Figure 4:
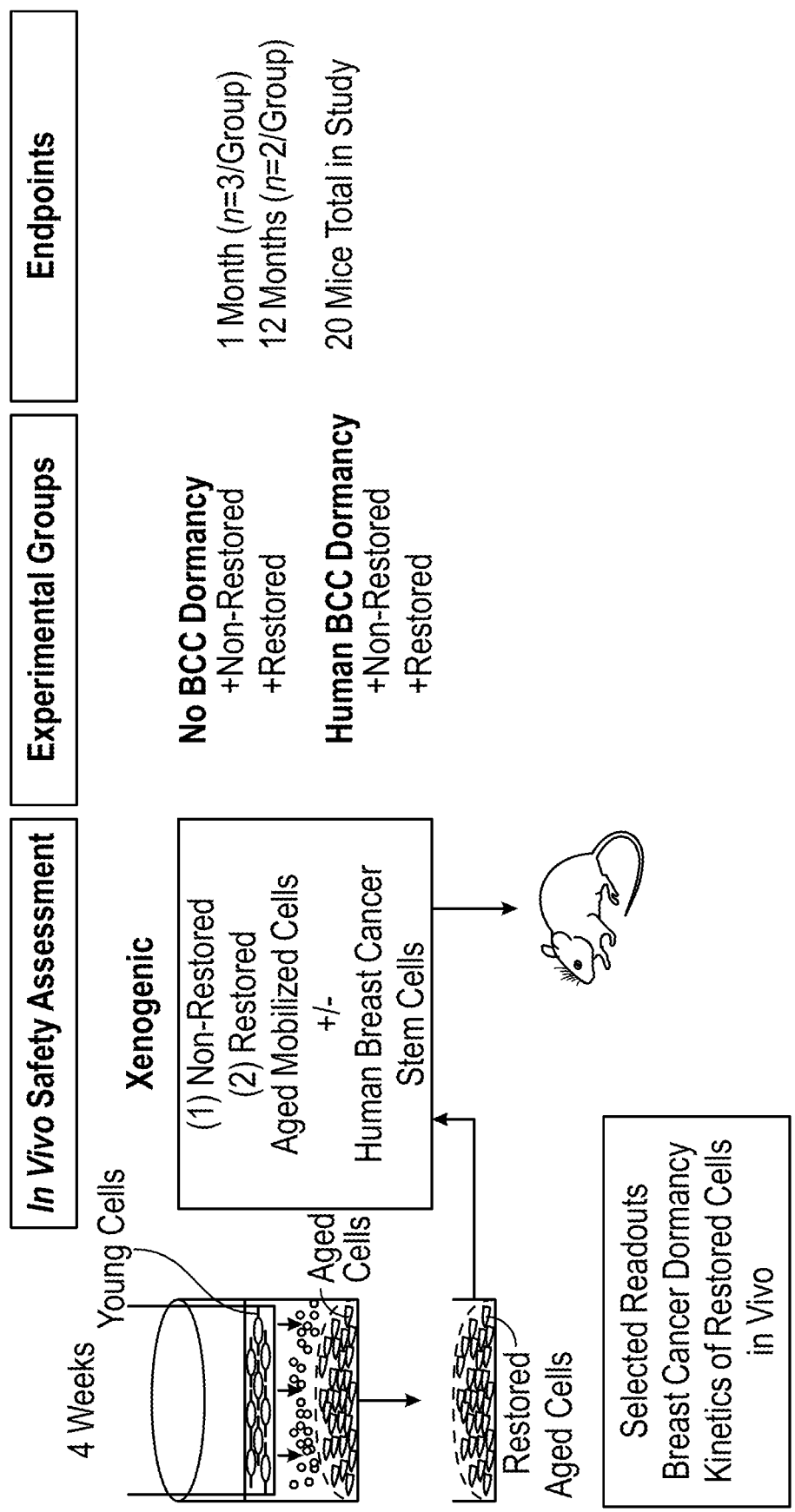
FIG. 4 is a depiction of the experimental design of a reprogrammed AASC nude mouse safety study.

To establish a breast cancer dormancy model for monitoring safety of the reprogrammed AASC, nude female BALB/c mice can be injected through intravenous route with $10^3$ human GFP+ breast cancer stem cells. The cancer stem cells can be injected in 100 uL of phosphate buffered saline (pH 7.4) or saline alone, via the tail vein. Breast cancer stem cells (CSCs) can be allowed to establish dormancy within the mice for 5 days. At day 6, reprogrammed or non-reprogrammed AASC can be injected intravenously in the following groups: Group 1: $10^7$ reprogrammed AASC; Group 2: $10^7$ baseline AASC cells (FIG. 4). These cells are generally comprised of immune cells, hematopoietic stem and progenitor cells, mesenchymal stem cells and endothelial progenitor cells.

Every 2 weeks, 0.2 mL of blood can be drawn from the tail vein to monitor the presence of human donor cells (CD45+) and breast cancer cells (anti-pan cytokeratin) by flow cytometry. The studies can be terminated at endpoints of 1 and 12 months. At the experimental endpoint, mice can be humanely euthanized with $CO_2$. Tissues can be taken from the bone marrow and major organs for histopathological analyses.

Example 4

Figure 5A:
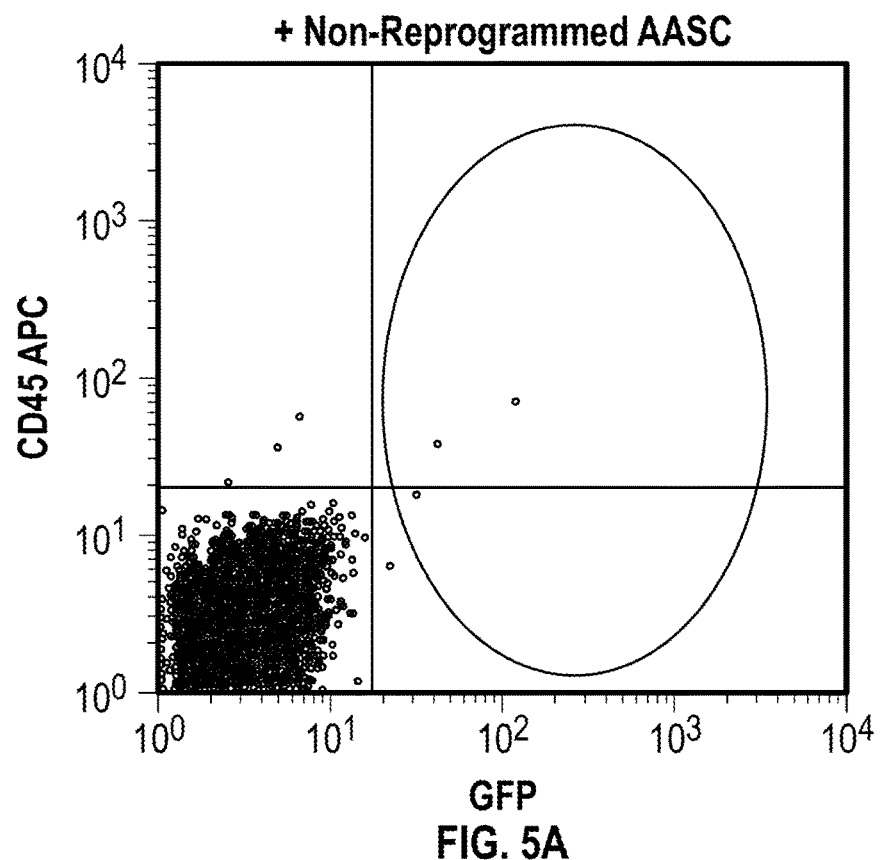
FIG. 5A depicts a dot plot of data generated by a flow cytometry experiment to monitor the presence of human breast cancer cells.
Figure 5B:
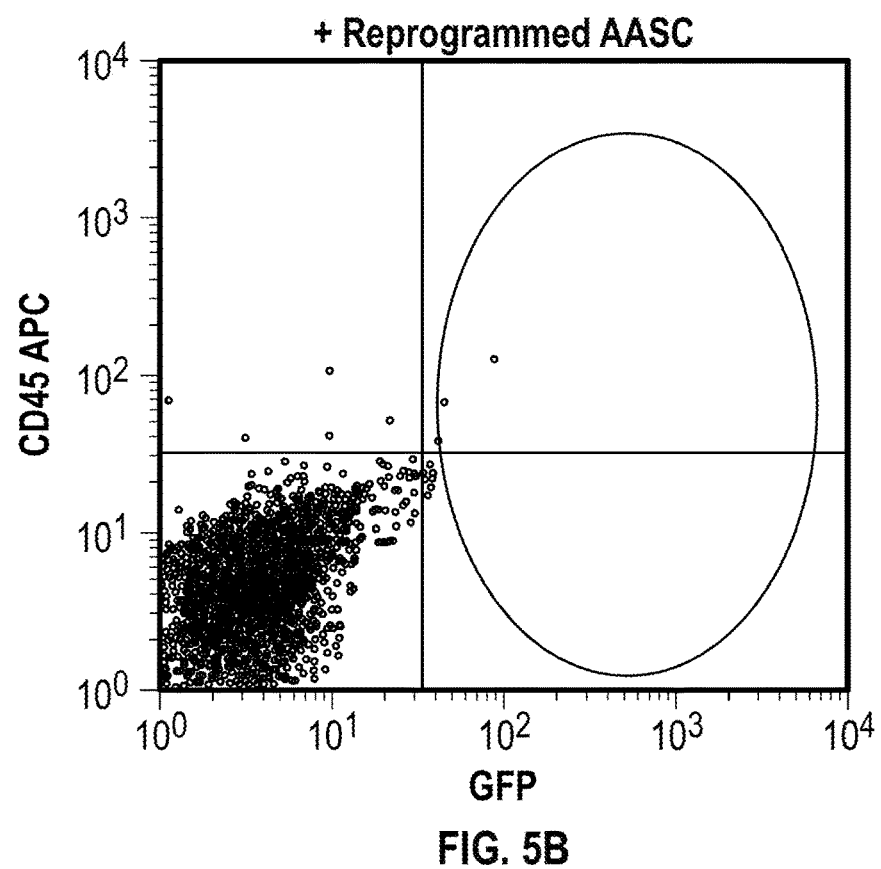
FIG. 5B depicts a dot plot of data generated by a flow cytometry experiment to monitor the presence of human breast cancer cells.
Figure 6A:
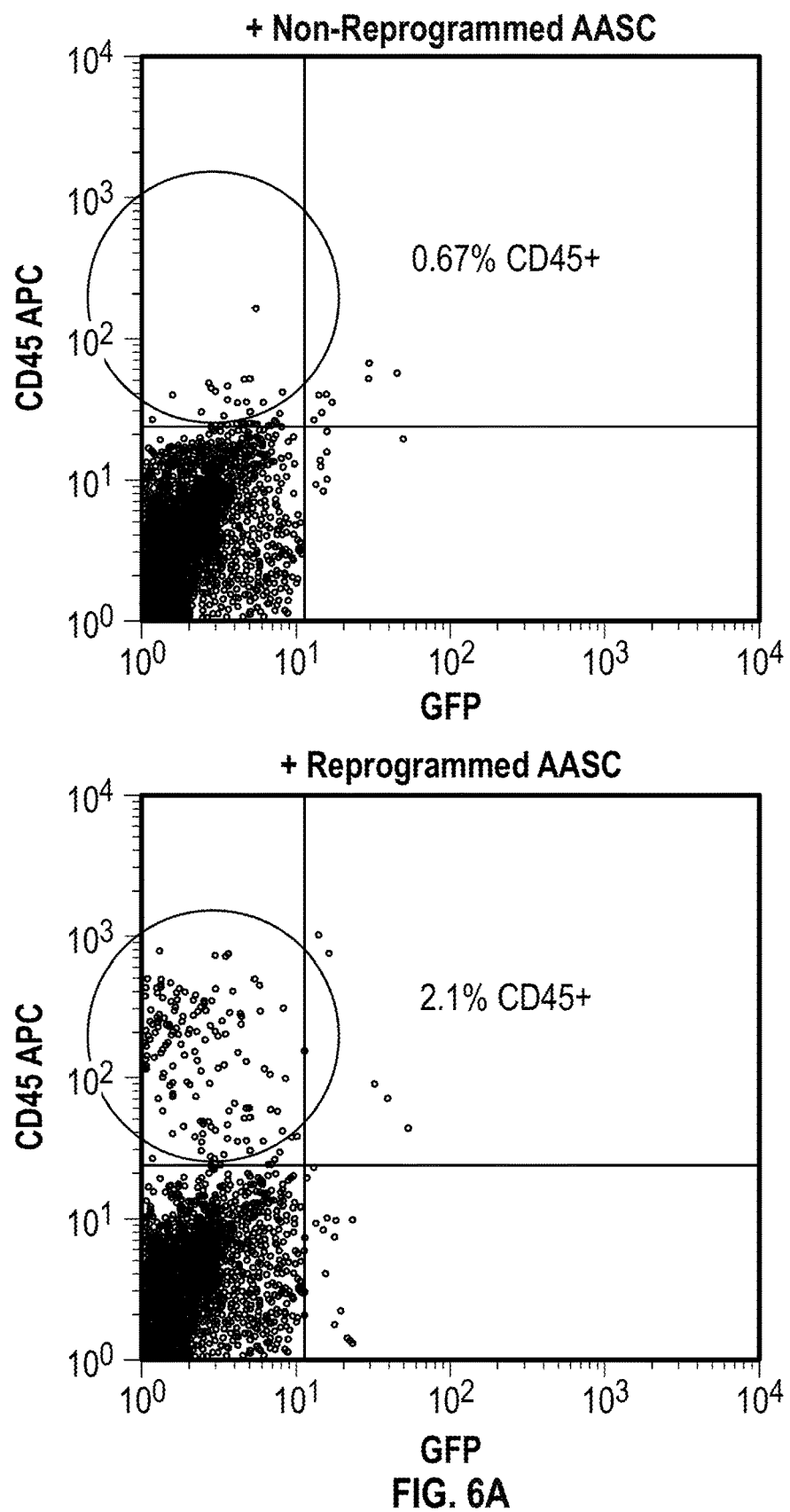
FIG. 6A depicts dot plots of data generated by a flow cytometry experiment to monitor the presence of non-reprogrammed and reprogrammed aged CD45+ human cells in mouse bone marrow.
Figure 6B:
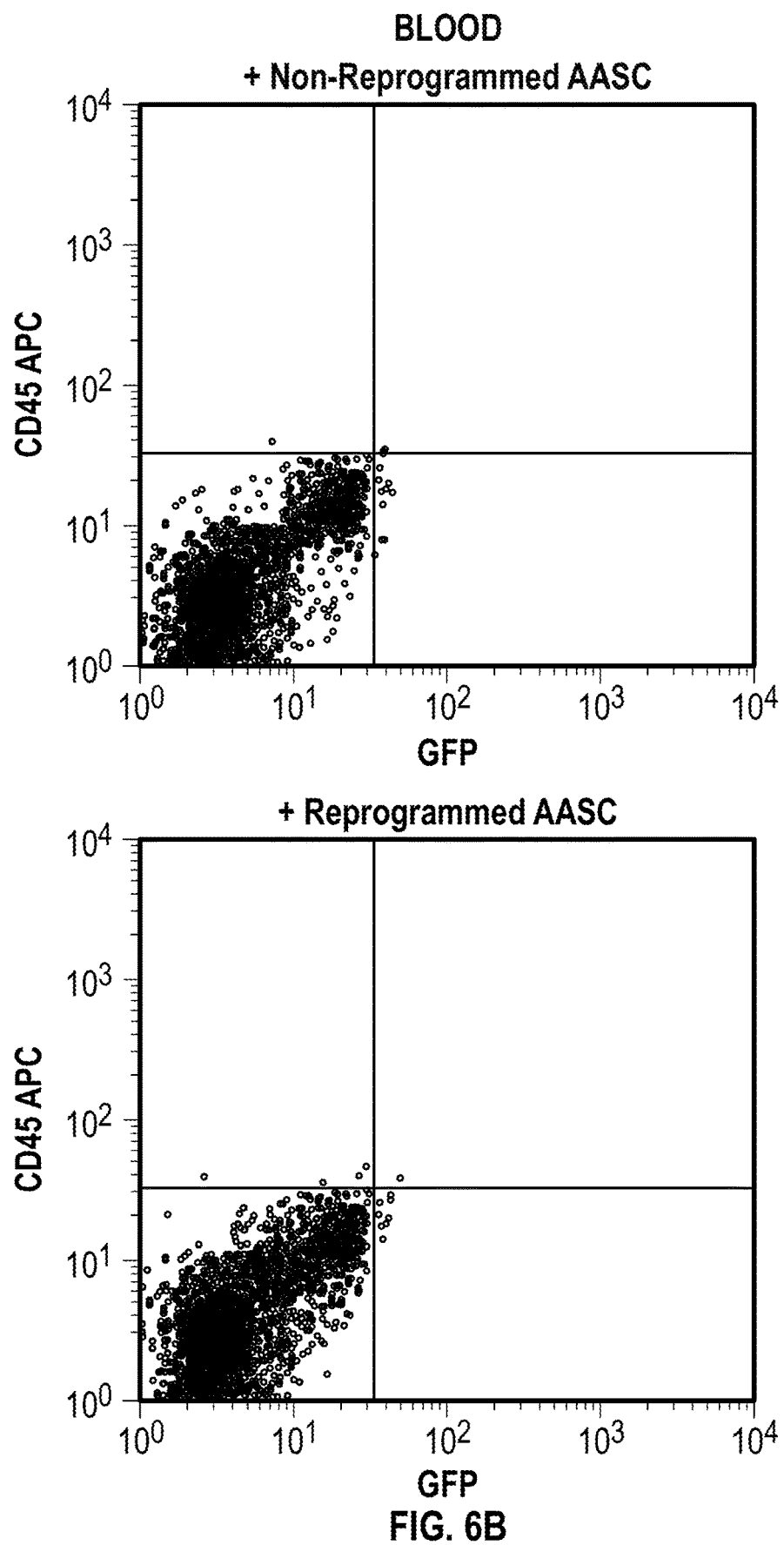
FIG. 6B depicts dot plots of data generated by a flow cytometry experiment to monitor the presence of non-reprogrammed and reprogrammed aged CD45+ human cells in mouse peripheral blood.
Figure 7A:
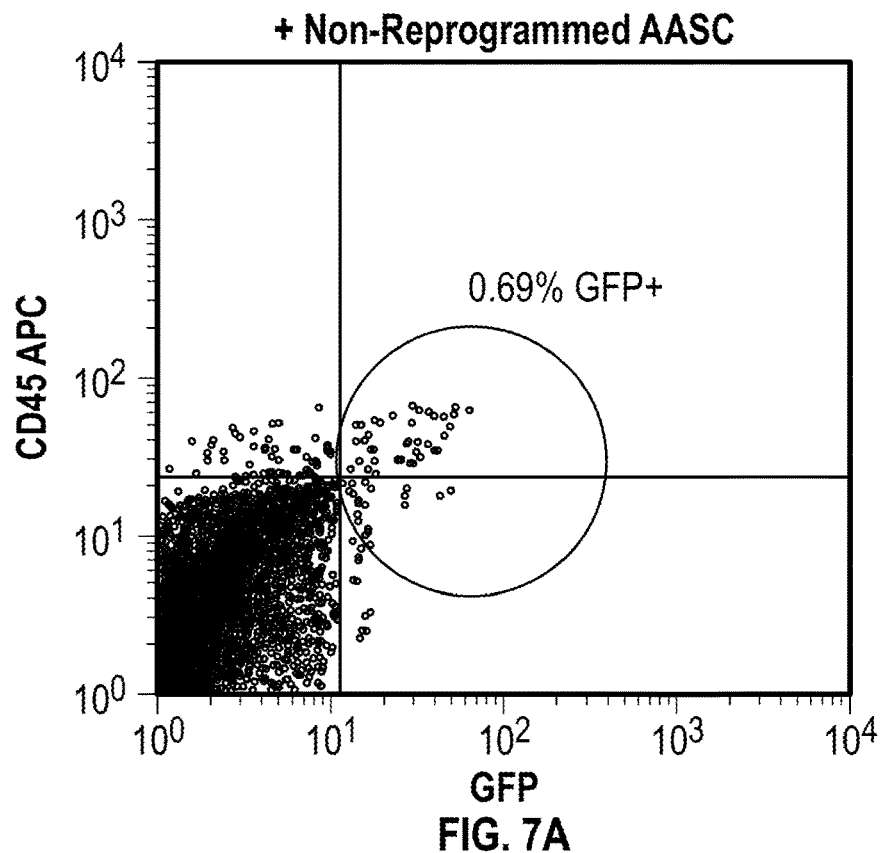
FIG. 7A depicts a dot plot of data generated by a flow cytometry experiment to monitor the presence of human breast cancer cells in bone marrow of mice.
Figure 7B:
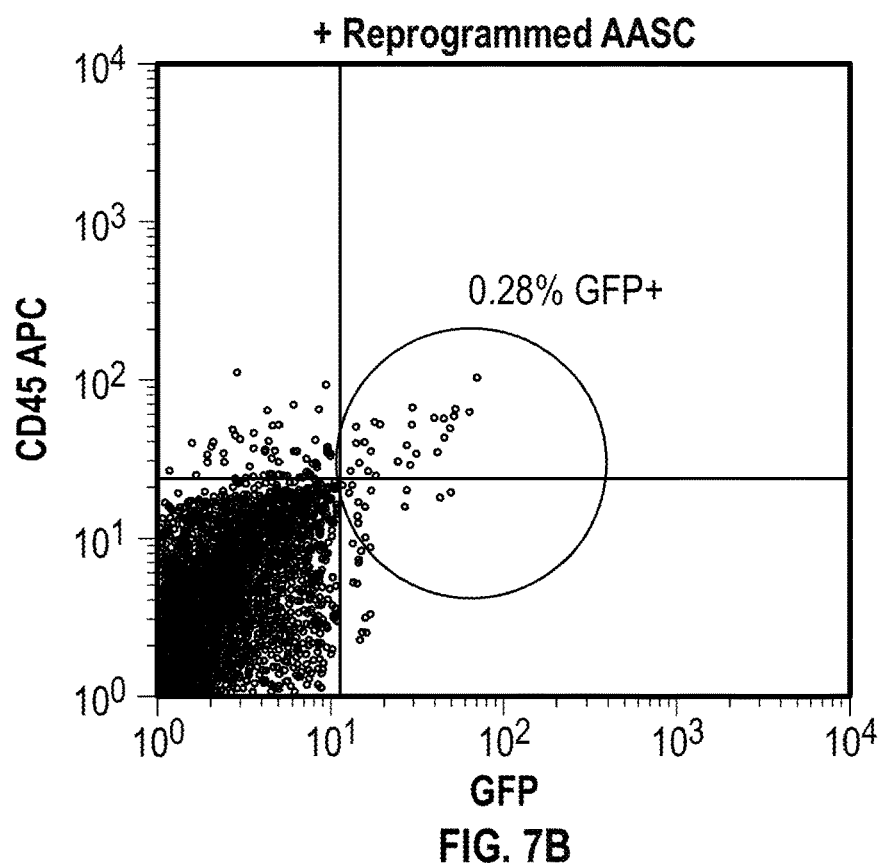
FIG. 7B depicts a dot plot of data generated by a flow cytometry experiment to monitor the presence of human breast cancer cells in bone marrow of mice.

At the first experimental endpoint of 1 month, mice were euthanized and peripheral blood was collected. No GFP+ cells (BCCs) were detected in the peripheral blood of either group by flow cytometry (FIGS. 5A-5B). Similar results were observed for cells expressing the human leukocyte marker CD45 (FIG. 6B).

Example 5

At the first experimental endpoint of 1 month bone marrow (BM) was also collected. Human CD45+ cells were detected in mouse BM, suggesting integration within the host microenvironment (FIG. 6A). Three times more CD45+ cells were identified in mouse BM infused with reprogrammed AASC compared to non-reprogrammed AASC. Assessment of mouse BM for GFP+ BCCs identified twice as many GFP+ cells in mice infused with non-reprogrammed AASC compared to reprogrammed AASC (FIGS.

7A-7B). These results suggest that the infused AASC also interact with the dormant BCCs in BM at 1 month.

Figures 8, 9:
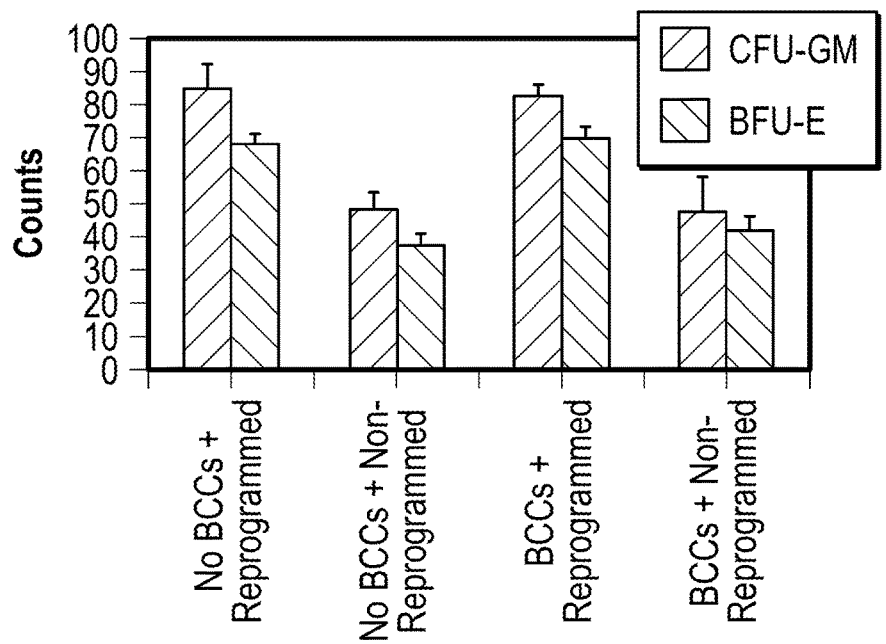
FIG. 8 is a bar chart depicting the results of a clonogenic assay from bone marrow of nude mice.
FIG. 9 is a depiction of a qPCR gene expression analysis.

The next set of studies investigated how the infused reprogrammed or non-reprogrammed AASC interact with the host bone marrow at the 1 month endpoint through use of a clonogenic assay to assess lineage-specific differentiation potential of hematopoietic stem cells (FIG. 8). The results suggest that reprogrammed AASC stimulate endogenous murine hematopoiesis, as indicated by the increased number of colony forming units (CFU) and blast forming units (BFU) for multiple hematopoietic lineages. These findings support the presently disclosed approach of reprogramming AASC through exposure to the ICM of YASC to promote youthful function of the aging immune system.

Example 6

Figure 10:
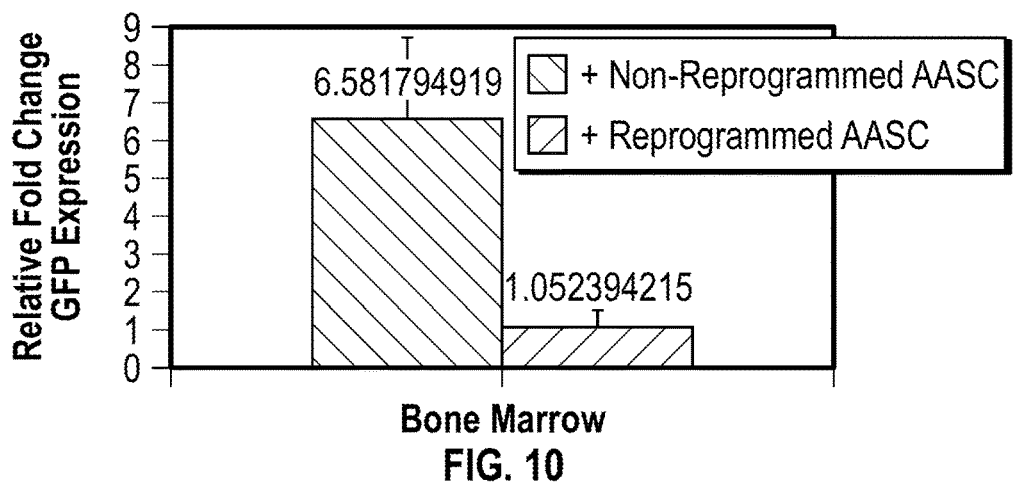
FIG. 10 is a bar chart depicting the results of a qPCR gene expression analysis for GFP expression in bone marrow of nude mice.

At the experimental endpoint of 1 month major organs were collected for detection of infused cells. Infused human cells were found in BM but no other major organs at 1 month (FIG. 9). Additionally, a greater number of total human AASC were found in BM of mice infused with reprogrammed AASC. A decreased number of BCCs was also observed in mice infused with reprogrammed AASC vs. non-reprogrammed AASC. A more detailed quantitative assessment of the levels of GFP+ cells detected in the mouse BM was performed using qPCR (FIG. 10). Six times more GFP mRNA expression was identified in mouse BM infused with non-reprogrammed AASC compared to reprogrammed AASC. GFP mRNA expression was undetectable in major organs.

Example 7

Figure 11A:
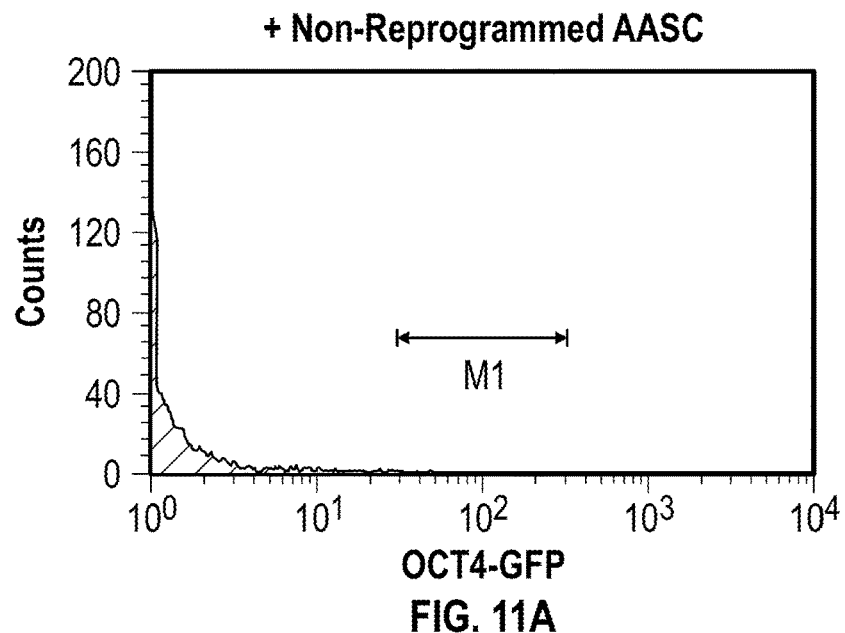
FIG. 11A depicts a histogram of data generated by a flow cytometry experiment to monitor the presence of human breast cancer cells in peripheral blood of mice.
Figure 11B:
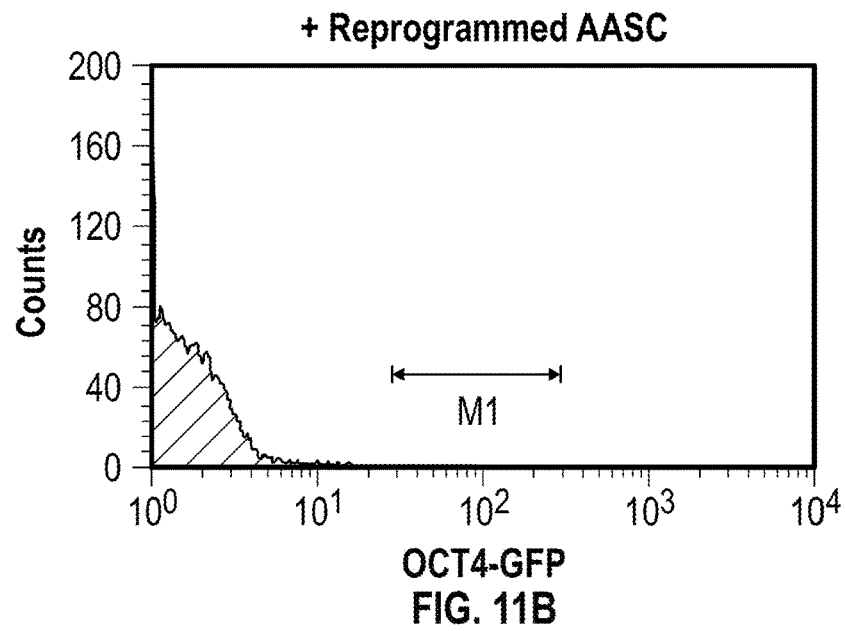
FIG. 11B depicts a histogram of data generated by a flow cytometry experiment to monitor the presence of human breast cancer cells in peripheral blood of mice.
Figure 12A:
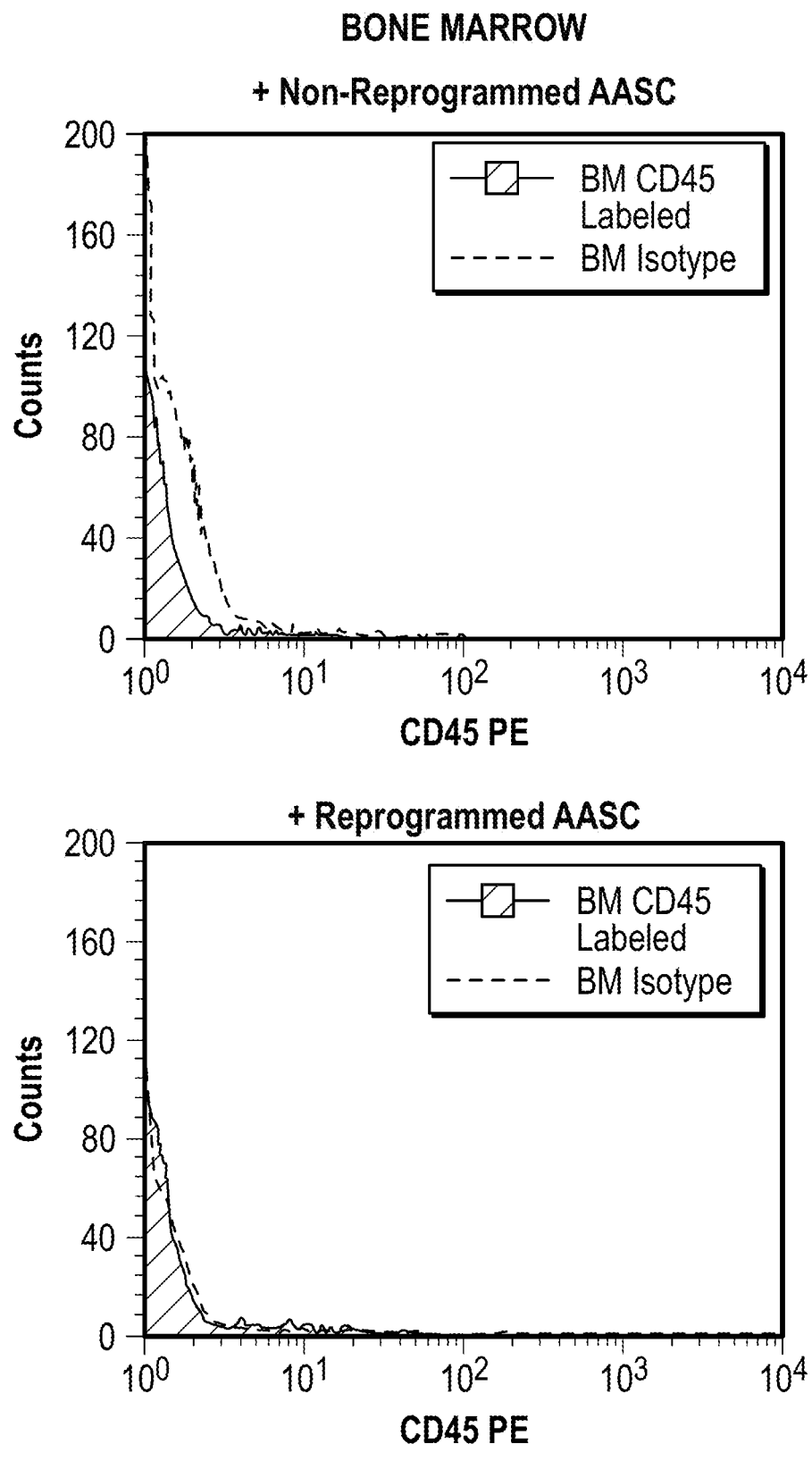
FIG. 12A depicts histograms of data generated by a flow cytometry experiment to monitor the presence of non-reprogrammed and reprogrammed aged CD45+ human cells in mouse bone marrow.
Figure 12B:
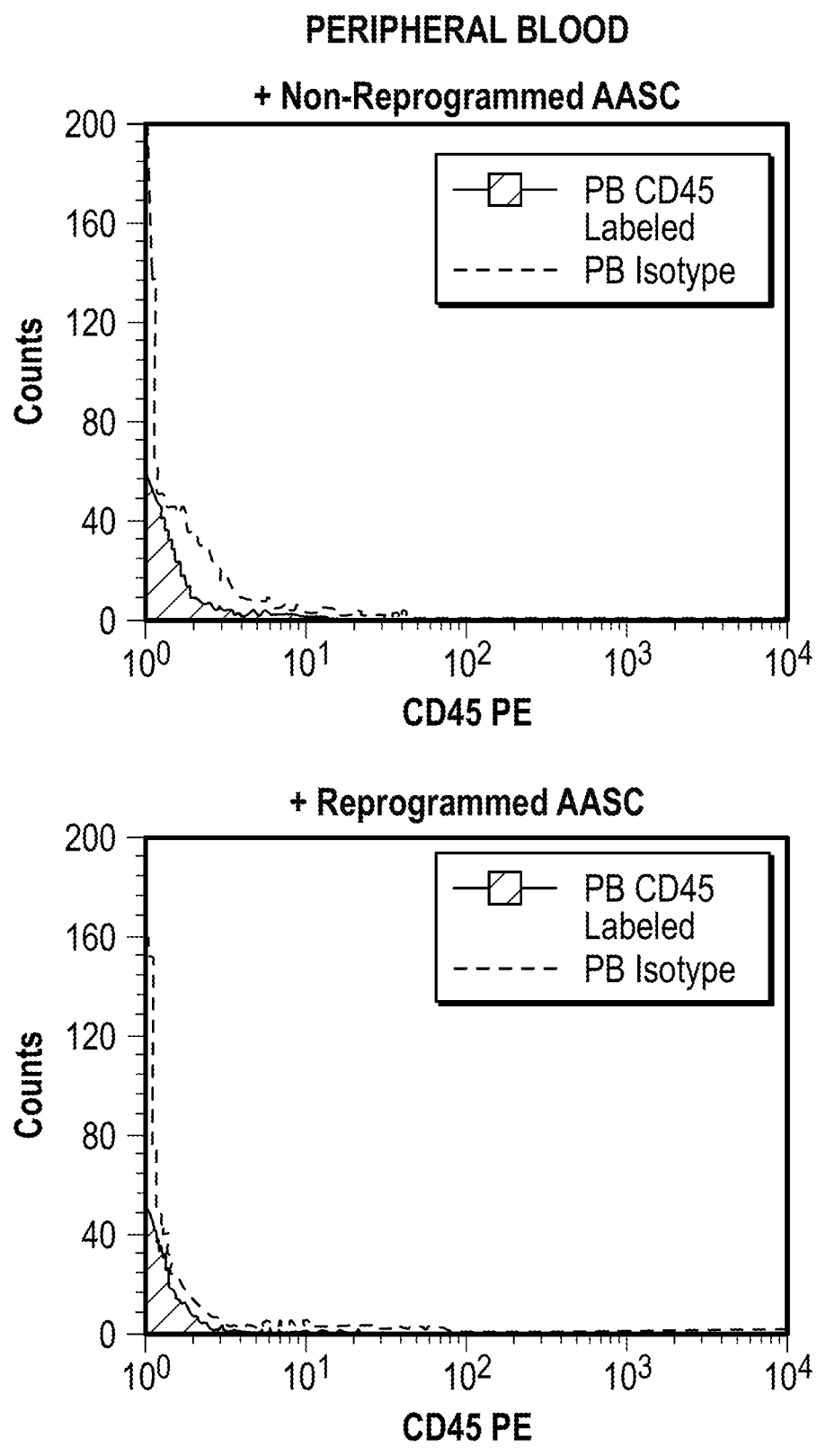
FIG. 12B depicts histograms of data generated by flow cytometry experiment to monitor the presence of non-reprogrammed and reprogrammed aged CD45+ human cells in mouse peripheral blood.

At the study endpoint of 12 months, mice were euthanized and peripheral blood was collected. No GFP+ cells were detected in peripheral blood of either group by flow cytometry (FIGS. 11A-11B). Similar results were observed for cells expressing the human leukocyte marker CD45 (FIG. 12B).

Example 8

Figure 13A:
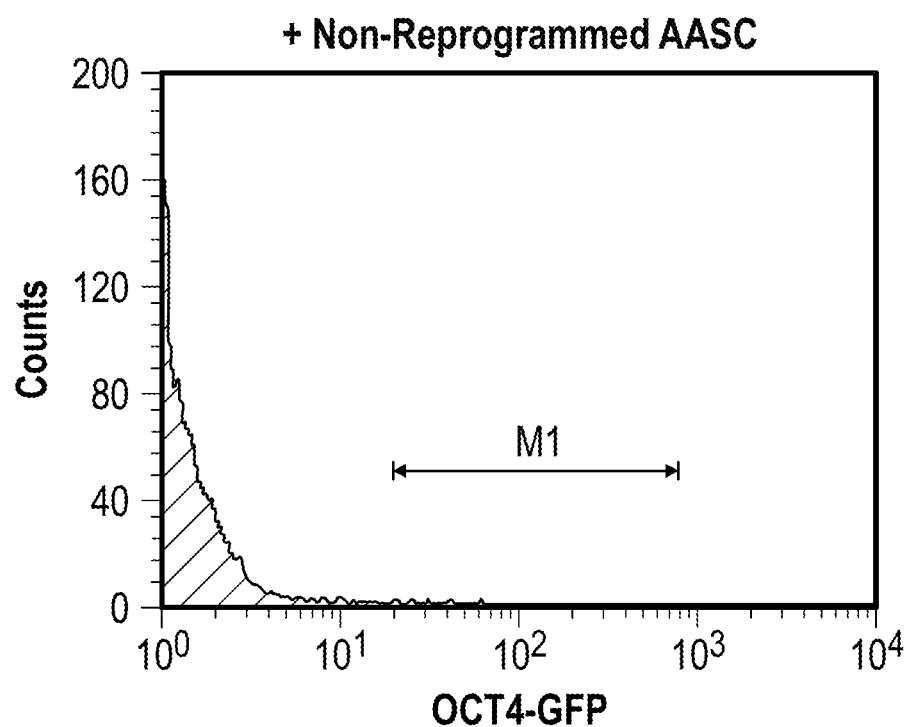
FIG. 13A depicts a histogram of data generated by a flow cytometry experiment to monitor the presence of human breast cancer cells in bone marrow of mice.
Figure 13B:
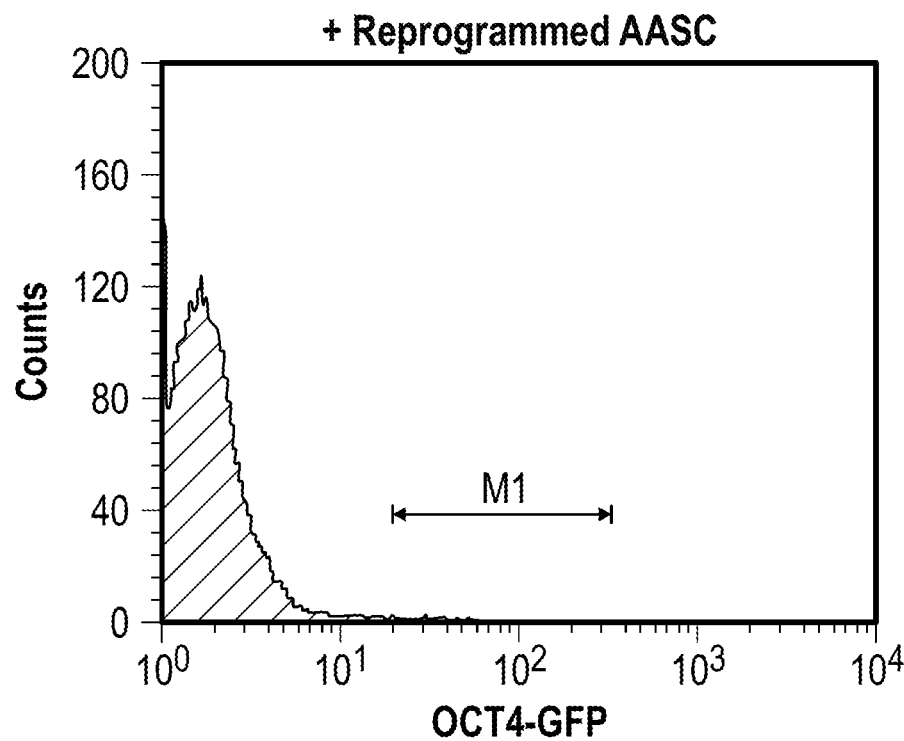
FIG. 13B depicts a histogram of data generated by a flow cytometry experiment to monitor the presence of human breast cancer cells in bone marrow of mice.

At the 12 month endpoint BM was also collected. Human CD45+ cells were not detected in mouse BM, suggesting that there was no long-term engraftment of the infused cells (FIG. 12A). Additionally, no GFP+ cells were found in the BM of mice infused with non-reprogrammed or reprogrammed AASC (FIGS. 13A-13B).

Figures 14, 15:
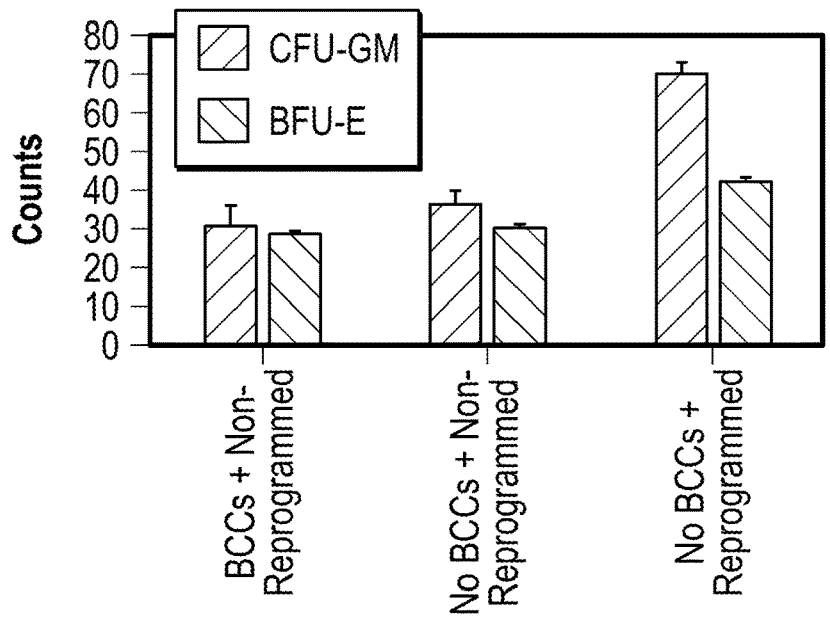
FIG. 14 is a bar chart depicting the results of a clonogenic assay from bone marrow of nude mice.
FIG. 15 is a depiction of a qPCR gene expression analysis.

The final set of BM studies again investigated functional hematopoiesis in the BM through use of a clonogenic assay. The results suggest that infusion of reprogrammed AASC maintain endogenous murine hematopoietic stimulation up to 12 months (FIG. 14). These findings are interesting, since the infused human cells are not detected at 12 months. These results suggest that the AASC infusions have long-term effects on endogenous hematopoiesis long after the cells have disappeared.

Example 9

At the study endpoint major organs were again collected for detection of infused cells. In contrast to the 1 month data for BM, at 12 months infused AASC were not found in BM or other major organs (FIG. 15). These data suggest no long-term engraftment of the infused human cells.

Example 10

Figure 16:
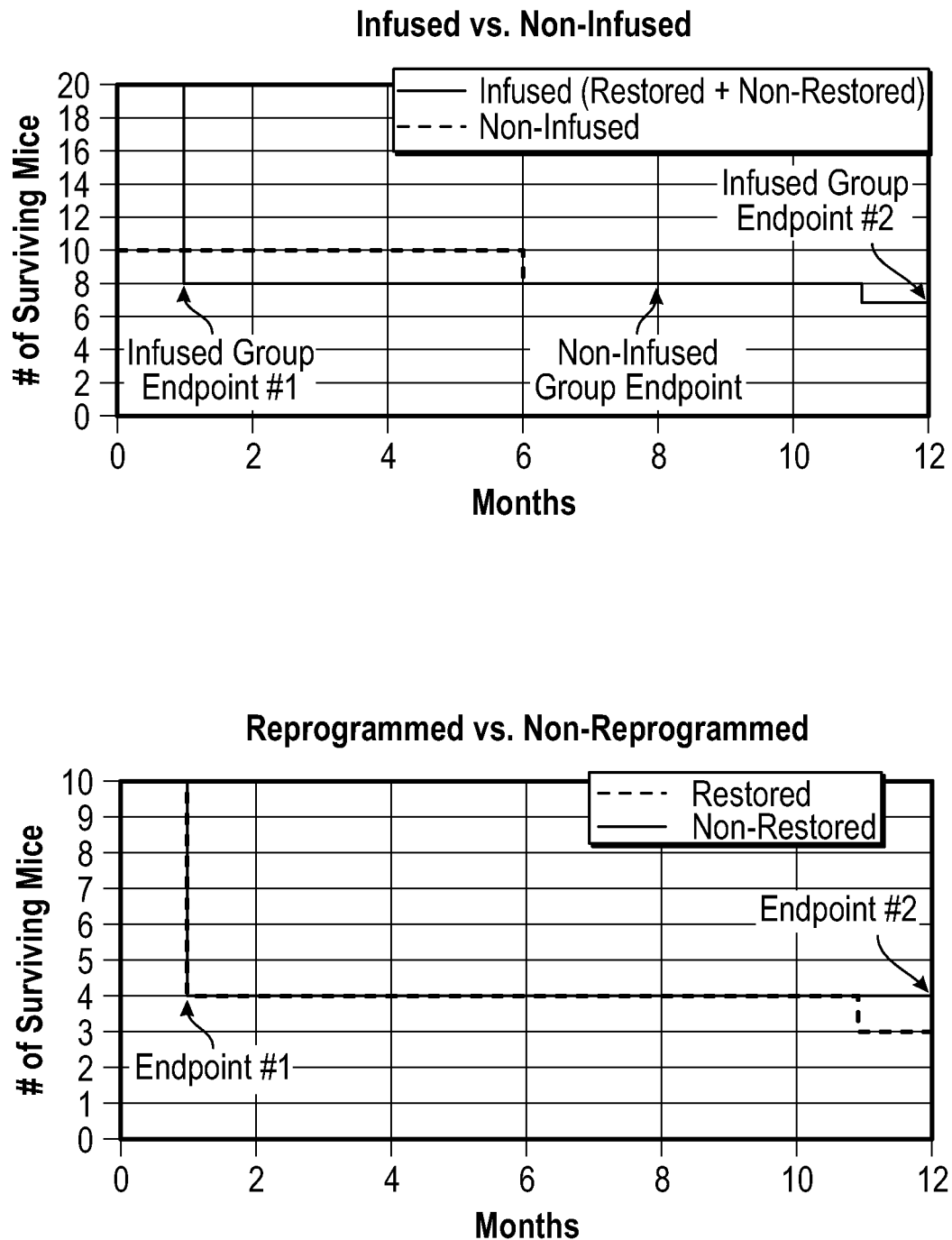
FIG. 16 is a Kaplan-Meier curve that depicts the number of mice from each of the main study groups.
Figure 16:
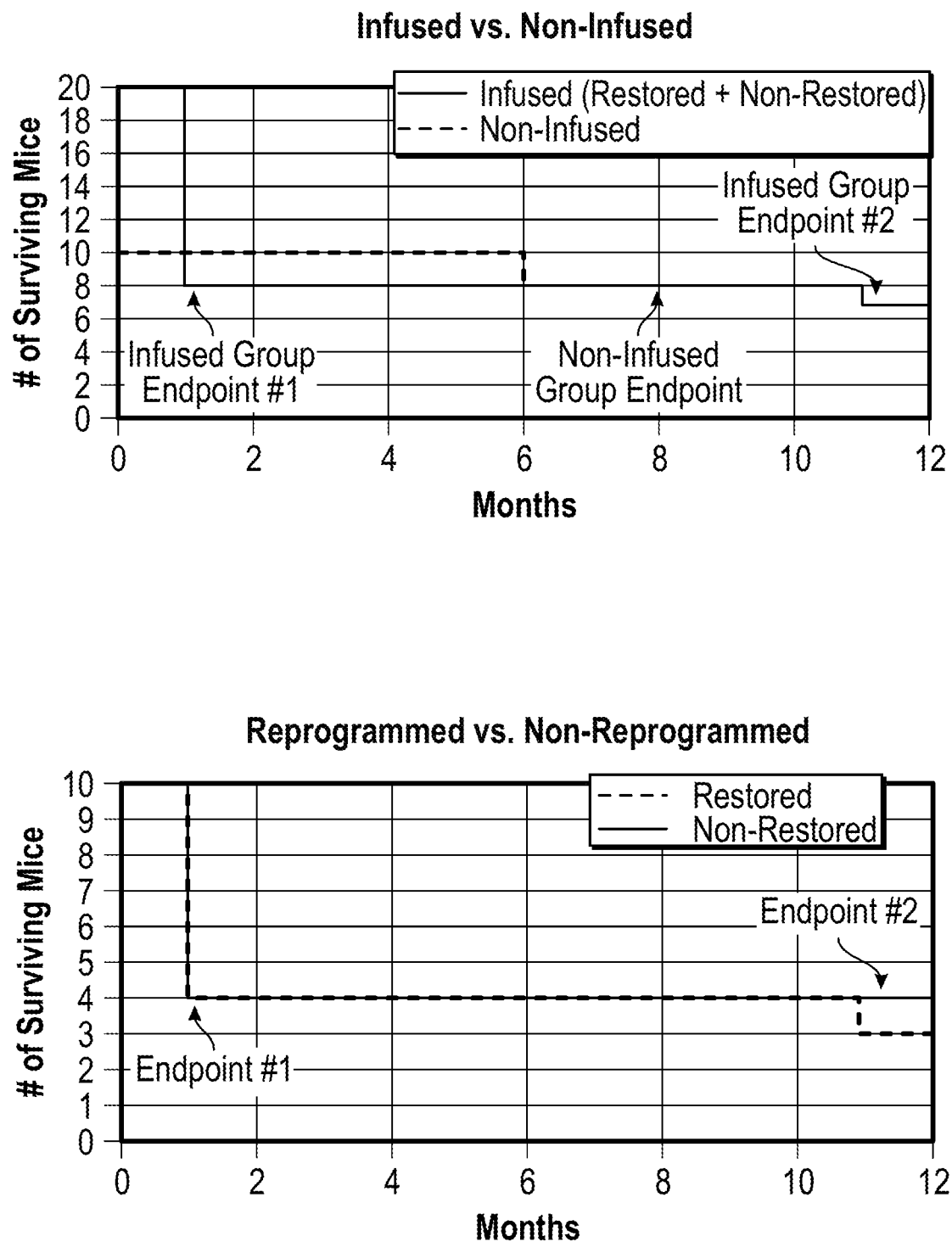

The final data generated at the study endpoint was a comparison of mouse survival rates in the different experimental groups. 20 nude mice had been infused with reprogrammed or non-reprogrammed AASC, 10 non-infused nude mice from a separate parallel study were used as control. 100% of mice infused with non-reprogrammed AASC were alive at the 12 month endpoint (4/4). 75% of mice infused with reprogrammed AASC were also alive (3/4) (FIG. 16). A parallel study utilizing control mice was completed at 8 months, with a survival rate of 80% (8/10). These results suggest that infusion with either non-reprogrammed or reprogrammed AASC improves survival compared to controls.

FIG. 17 is a descriptive list of attributes used to test for AASC reprogramming that compares nude mouse xenograft study readouts among groups infused with non-reprogrammed or reprogrammed AASC.

The following enumerated embodiments are provided as non-limiting examples.

A first embodiment which is a method comprising (a) obtaining young adult stem cells (YASC) from a first subject; (b) lysing the YASC to generate a lysate comprising an intracellular matrix (ICM) and other cellular components; (c) filtering the lysate through a filter having a membrane size of equal to or less than 0.4 micron to obtain a filtrate; and (d) applying the filtrate to a culture of aged adult stem cells (AASC) for a time period ranging from about 24 hours to about 14 days to generate a reprogrammed AASC (R-AASC) wherein the AASC were obtained from a second subject and wherein the R-AASC when infused into a breast cancer stem model results in a reduced number of breast cancer cells in bone marrow in comparison to a breast cancer stem model having AASC that have not been reprogrammed.

A second embodiment which is the method of the first embodiment wherein the breast cancer stem model comprises nude BALB/c mice.

A third embodiment which is the method of the second embodiment wherein the breast cancer stem model is established through the introduction of equal to or greater than about $10^3$ subject breast cancer stem cells into the nude BALB/c mice.

A fourth embodiment which is the method of any of the first through third embodiments further comprising determining alterations in gene expression levels for the R-AASC for at least 10 age-related genes selected from the group consisting of C-abl oncogene-1 non-receptor tyrosine kinase; V-akt murine thymona viral oncogene homolog 1; aldehyde dehydrogenase 1 family, member A3; Ataxia telangiectasia mutated; BMI1 polycomb ring finger oncogene; calrecticulin; cyclin A2; cyclin B1; cyclin D1; cyclin E1; CD44 molecule, cell division cycle 25 homolog C; cyclin-dependent kinase 2; cyclin-dependent kinase 4; cyclin-dependent kinase 6; cyclin-dependent kinase inhibitor 1A; cyclin-dependent kinase inhibitor 1B; cyclin-dependent kinase inhibitor 1C; cyclin-dependent kinase inhibitor 2A; cyclin-dependent kinase inhibitor 2B; cyclin-dependent kinase inhibitor 2C; and cyclin-dependent kinase inhibitor 2D.

A fifth embodiment which is the method of any of the first through fourth embodiments wherein the young adult stem cells are collected from a subject having a chronological age of equal to or less than 40 years.

A sixth embodiment which is the method of any of the first through fifth embodiments wherein the first subject and second subject are related by consanguinity.

A seventh embodiment which is the method of any of the first through sixth embodiments wherein the first subject and second subject are the same.

An eighth embodiment which is the method of any of the first through seventh embodiments wherein the first subject and second subject are different.

A ninth embodiment which is the method of any of the first through eighth embodiment wherein the YASC, the AASC, or both were stored for a time period of from about 24 hours to about 20 years prior to step (a).

A tenth embodiment which is the method of any of the first through ninth embodiments further comprising administering the filtrate to the second subject.

An eleventh embodiment which is the method comprising (a) collecting young adult stem cells (YASC) from a first subject having a chronological age of less than about 40 years; (b) lysing the YASC to generate a mixture; (c) filtering the mixture through a size-selective membrane to produce a reprogramming solution; and (d) contacting the reprogramming solution with a culture of aged adult stem cells (AASC) for a time period of from about 24 hours to about 14 days to produce reprogrammed AASC (R-AASC) wherein the R-AASC have an increase in expression of calreticulin and galactosidase-β1 of equal to or greater than about 1.5 fold when compared to the AASC.

A twelfth embodiment which is the method of the eleventh embodiment wherein the reprogramming solution is administered to a second subject.

A thirteenth embodiment which is the method of the twelfth embodiment wherein the second subject has at least one characteristic selected from the group consisting of: having a disease state not present in or not diagnosed in the first subject; having a chronological age of greater than about 40 years; and being related to the first subject by consanguinity.

A fourteenth embodiment which is the method of the twelfth embodiment wherein the first subject and second subject are the same.

A fifteenth embodiment which is the method of the twelfth embodiment wherein the first subject and second subject are different.

A sixteenth embodiment which is the method of the twelfth embodiment wherein the first subject and second subject are related by consanguinity.

A seventeenth embodiment which is the method of any of the eleventh through sixteenth embodiments further comprising contacting the reprograming solution with manumycin prior to step (c) to produce a deactivated reprogramming solution.

An eighteenth embodiment which is the method of any of the eleventh through seventeenth embodiments wherein the deactivated reprogramming solution when contacted with a AASC for a time period of from 24 hours to 14 days does not result in an increase in expression of calreticulin and galactosidase-β1 of equal to or greater than about 1.5 fold.

A nineteenth embodiment which is the method of any of the eleventh through eighteenth embodiments wherein the YASC, the AASC, or both were stored for a time period of from about 24 hours to about 20 years prior to step (a).

A twentieth embodiment which is the method of any of the eleventh through nineteenth embodiments wherein the R-AASC is administered to a third subject in need thereof.

The invention claimed is:

1. A method comprising;
   (a) obtaining mobilized peripheral blood mononuclear cells comprising young adult stem cells (YASC) from a first subject wherein the first subject has a chronological age of less than about 30 years and wherein the YASC comprise immune cells, hematopoietic stem cells, hematopoietic progenitor cells, mesenchymal stem cells, endothelial progenitor cells or combinations thereof;
   (b) lysing the mobilized peripheral blood mononuclear cells comprising YASC to generate a lysate comprising an intracellular matrix (ICM) and other cellular components, wherein lysing comprises physiological rupture, and wherein the other cellular components comprise cells and/or apoptotic bodies;
   (c) passively filtering the lysate through a filter having a pore size of 0.4 micron to obtain a cell-free filtrate, wherein the cell-free filtrate comprises at least a portion of the ICM; and
   (d) applying the cell-free filtrate to a culture of mobilized peripheral blood mononuclear cells comprising aged adult stem cells (AASC) for a time period ranging from about 24 hours to about 30 days to generate a reprogrammed AASC (R-AASC),
   wherein the AASC were obtained from a second subject and comprise immune cells, hematopoietic stem cells, hematopoietic progenitor cells, mesenchymal stem cells, endothelial progenitor cells or combinations thereof; and
   wherein the second subject has a chronological age of equal to or greater than about 40 years and wherein the R-AASC have a decrease in expression of cyclin-dependent kinase inhibitor 2A (CDKN2A) equal to or greater than about 1.5 fold when compared to the AASC.

2. The method of claim 1 further comprising determining alterations in gene expression levels for the R-AASC for at least 10 age-related genes selected from the group consisting of galactosidase-β1; C-abl oncogene-1 non-receptor tyrosine kinase; V-akt murine thymoma viral oncogene homolog 1; aldehyde dehydrogenase 1 family, member A3; Ataxia telangiectasia mutated; BMI1 polycomb ring finger oncogene; calreticulin; cyclin A2; cyclin B1; cyclin D1; cyclin E1; CD44 molecule, cell division cycle 25 homolog C; cyclin-dependent kinase 2; cyclin-dependent kinase 4; cyclin-dependent kinase 6; cyclin-dependent kinase inhibitor 1A; cyclin-dependent kinase inhibitor 1B; cyclin-dependent kinase inhibitor 1C; cyclin-dependent kinase inhibitor 2B; cyclin-dependent kinase inhibitor 2C; and cyclin-dependent kinase inhibitor 2D.

3. The method of claim 1 wherein the first subject and second subject are related by consanguinity.

4. The method of claim 1 wherein the first subject and second subject are the same, and wherein the YASC and the AASC are not harvested on the same day.

5. The method of claim 1 wherein the first subject and second subject are different.

6. The method of claim 1 wherein the YASC, the AASC, or both were stored for a time period of from about 24 hours to about 20 years prior to step (a).

7. The method of claim 1, wherein the cell-free filtrate further comprises exosomes.

8. A method comprising;
   (a) collecting mobilized peripheral blood mononuclear cells comprising a first population of adult stem cells from a first subject having a chronological age of less than about 30 years wherein the first population of adult stem cells comprises immune cells, hematopoietic stem cells, hematopoietic progenitor cells, mesenchymal stem cells, endothelial progenitor cells or combinations thereof;
(b) lysing the mobilized peripheral blood mononuclear cells comprising YASC to generate a mixture, wherein lysing comprises physiological rupture, wherein the mixture comprises an intracellular matrix (ICM) and other cellular components, and wherein the other cellular components comprise cells and/or apoptotic bodies;
(c) passively filtering the mixture through a membrane having a pore size of 0.4 micron to produce a cell-free solution, wherein the cell-free reprogramming solution comprises at least a portion of the ICM; and
(d) contacting the cell-free solution with a culture of mobilized peripheral blood mononuclear cells comprising a second population of adult stem cells for a time period of from about 24 hours to about 14 days to produce reprogrammed adult stem cells wherein the reprogrammed adult stem cells comprise immune cells, hematopoietic stem cells, hematopoietic progenitor cells, mesenchymal stem cells, endothelial progenitor cells or combinations thereof;
wherein the reprogrammed adult stem cells have a decrease in expression of cyclin-dependent kinase inhibitor 2A (CDKN2A) of equal to or greater than about 1.5 fold when compared to the second population of adult stem cells; and
wherein the second population of adult stem cells is obtained from a subject having a chronological age of equal to or greater than about 40 years.

9. The method of claim 8 wherein the second subject has at least one characteristic selected from the group consisting of: having a disease state not present in or not diagnosed in the first subject and being related to the first subject by consanguinity.

10. The method of claim 8 wherein the first subject and second subject are the same, and wherein the first population of adult stem cells and the second population of adult stem cells are not harvested on the same day.

11. The method of claim 8 wherein the first subject and second subject are different.

12. The method of claim 8 wherein the first subject and second subject are related by consanguinity.

13. The method of claim 8 wherein the first population of adult stem cells, the second population of adult stem cells, or both were stored for a time period of from about 24 hours to about 20 years prior to step (a).

14. The method of claim 8 wherein the reprogrammed adult stem cells are administered to a third subject in need thereof.

15. The method of claim 8, wherein the first population of adult stem cells are present in an amount of about $1 \times 10^7$ cells.

16. The method of claim 8, wherein the cell-free solution further comprises exosomes.

17. A method comprising:
(a) collecting mobilized peripheral blood mononuclear cells comprising a first population of adult stem cells from a first subject having a chronological age of less than about 30 years, wherein the first population of adult stem cells comprises immune cells, hematopoietic stem cells, hematopoietic progenitor cells, mesenchymal stem cells, endothelial progenitor cells or combinations thereof;
(b) lysing the mobilized peripheral blood mononuclear cells comprising the first population of adult stem cells to generate a lysate, wherein lysing comprises physiological rupture, wherein the lysate comprises an intracellular matrix (ICM);
(c) passively filtering out material larger than 0.4 microns from the lysate to obtain a cell-free filtrate, wherein the cell-free filtrate comprises at least a portion of the ICM; and
(d) contacting the filtrate with a culture of mobilized peripheral blood mononuclear cells comprising a second population of adult stem cells obtained from a subject having a chronological age of equal to or greater than about 40 years for a time period of from about 24 hours to about 14 days;
wherein the second population of adult stem cells after the contacting of step (d) have a decrease in expression of cyclin-dependent kinase inhibitor 2A (CDKN2A) equal to or greater than about 1.5 fold when compared to the second population of adult stem cells prior to the contacting of step (d).

18. Reprogrammed adult stem cells made by a method comprising:
(a) collecting mobilized peripheral blood mononuclear cells comprising a first population of adult stem cells from a first subject having a chronological age of less than about 30 years, wherein the first population of adult stem cells comprises immune cells, hematopoietic stem cells, hematopoietic progenitor cells, mesenchymal stem cells, endothelial progenitor cells or combinations thereof;
(b) lysing the mobilized peripheral blood mononuclear cells comprising the first population of adult stem cells to generate a lysate, wherein lysing comprises physiological rupture, wherein the lysate comprises an intracellular matrix (ICM);
(c) passively filtering out material larger than 0.4 microns from the lysate to obtain a cell-free filtrate, wherein the cell-free filtrate comprises at least a portion of the ICM; and
(d) contacting the filtrate with a culture of mobilized peripheral blood mononuclear cells comprising a second population of adult stem cells obtained from a subject having a chronological age of equal to or greater than about 40 years for a time period of from about 24 hours to about 14 days to produce the reprogrammed adult stem cells,
wherein the reprogrammed adult stem cells comprise immune cells, hematopoietic stem cells, hematopoietic progenitor cells, mesenchymal stem cells, endothelial progenitor cells or combinations thereof; and
wherein the reprogrammed adult stem cells have a decrease in expression of cyclin-dependent kinase inhibitor 2A (CDKN2A) equal to or greater than about 1.5 fold when compared to the second population of adult stem cells.

* * * * *